(12) United States Patent
Gellman et al.

(10) Patent No.: US 9,255,122 B2
(45) Date of Patent: Feb. 9, 2016

(54) CHOLATE AND DEOXYCHOLATE-BASED AMPHIPHILES FOR MEMBRANE PROTEIN MANIPULATION

(71) Applicant: Wisconsin Alumni Research Foundation, Madison, WI (US)

(72) Inventors: Samuel Helmer Gellman, Madison, WI (US); Pil Seok Chae, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/556,544

(22) Filed: Dec. 1, 2014

(65) Prior Publication Data

US 2015/0203441 A1    Jul. 23, 2015

Related U.S. Application Data

(60) Provisional application No. 61/910,574, filed on Dec. 2, 2013.

(51) Int. Cl.
| | | |
|---|---|---|
| C07C 257/00 | (2006.01) | |
| C07C 263/00 | (2006.01) | |
| C07K 1/14 | (2006.01) | |
| C07J 41/00 | (2006.01) | |

(52) U.S. Cl.
CPC ... *C07K 1/14* (2013.01); *C07J 41/00* (2013.01)

(58) Field of Classification Search
None
See application file for complete search history.

(56) References Cited

U.S. PATENT DOCUMENTS

| | | |
|---|---|---|
| 6,172,262 B1 | 1/2001 | McQuade et al. |
| 8,263,754 B2 | 9/2012 | Gellman et al. |
| 2009/0270598 A1 | 10/2009 | Gellman et al. |
| 2010/0311956 A1 | 12/2010 | Gellman et al. |

OTHER PUBLICATIONS

Breyton et al., Hemifluorinated surfactants: a non-dissociating environment for handling membrane proteins in aqueous solutions?, *FEBS Lett.* 2004, 564, 312.
Carey, F. and Sundberg, R., *Advanced Organic Chemistry, Part B: Reactions and Synthesis*, 5th Ed., Plenum: New York, © 2008, ISBN 978-0387683546 (Book).
Chae et al., Glycotripod Amphiphiles for Solubilization and Stabilization of a Membrane-Protein Superassembly: Importance of Branching in the Hydrophilic Portion, *ChemBioChem* 2008, 9, 1706-1709.
Chae et al.; Tripod Amphiphiles for Membrane Protein Manipulation, *Mol. BioSyst.* 2010, 6, 86-94.
Chae et al., Tandem Facial Amphiphiles for Membrane Protein Stabilization, *J. Am. Chem. Soc.* 2010, 132, 16750-16752.
Chae et al., Maltose-neopentyl glycol (MNG) amphiphiles for solubilization, stabilization and crystallization of membrane proteins, *Nat. Methods* 2010, 7, 1003-1008.
Chae et al., Crystallographic Characterization of N—Oxide Tripod Amphiphiles, *J. Am. Chem. Soc.* 2010, 132, 1953-1959.
Chae et al., A New Class of Amphiphiles Bearing Rigid Hydrophobic Groups for Solubilization and Stabilization of Membrane Proteins, *Chem.-Eur. J.* 2012, 18, 9485-9490.
Chae et al., Glucose-Neopentyl Glycol (GNG) Amphiphiles for Membrane Protein Solubilization, Stabilization and Crystallization, *Chem. Comm.* 2013, 49, 2287-2289.
Chae et al., Carbohydrate-containing Triton X-100 Analogous for Membrane Protein Solubilization and Stabilization, *Mol. BioSyst.* 2013, 9, 626-629.
Chang et al., Structure of the MscL Homolog from *Mycobacterium tuberculosis*: A Gated mechanosensitive Ion Channel, *Science*, 1998, 282: 2220-2226.
Cho et al., Hemifluorinated Maltose-Neopentyl Glycol (HF-MNG) Amphiphiles for Membrane Protein Stabilisation, *ChemBioChem* 2013, 14, 452-455.
Gellman et al., Rigid Amphiphiles for Membrane Protein Manipulation, *Angew. Chem. Int. Ed.* 2000, 39, 758.
Gellman et al., Glycotripod Amphiphiles for Solubilization and Stabilization of a Membrane Protein Superassembly: Importance of Branching in the Hydrophilic Portion, *ChemBioChem* 2008, 9, 1706-1709.
Goldsmith et al., Rapid isolation of bacterial photosynthetic reaction centers with an engineered poly-histidine tag, *Biochimica et Biophysica Acta.*, 1996, 1276: 171-175.
*Greene's Protective Groups in Organic Synthesis, 4th Edition*, Peter G. M. Wuts and Theodora W. Greene, ISBN: 978-0-471-69754-1, © 2006, John Wiley & Sons, Inc., New York, NY In particular, see Chapter 1 (The Role of Protective Groups in Organic Synthesis), Chapter 2 (Protection for the Hydroxyl Group, Including 1,2- and 1,3-Diols), Chapter 4 (Protection for the Carbonyl Group), Chapter 5 (Protection for the Carboxyl Group), and Chapter 10 (Reactivities, Reagents, and Reactivity Charts) (Book).
Hermanson, Greg T., in *Bioconjugate Techniques* (Academic Press, San Diego, CA 1996 (Book).
Hjelmeland, The Design and Synthesis of Detergents for Membrane Chemistry, *Methods in Enzymology*, 1986, vol. 124; 135-164.
Hovers et al., A class of mild surfactants that keep integral membrane proteins water-soluble for functional studies and crystallization, *Mol. Membr. Biol.* 2011, 28, 170-180.
Howell et al., Chobimalt: A Cholesterol-Based Detergent, *Biochemistry* 2010, 49, 9572-9583.
Kirmaier et. al., Comparisons of M-Side Electron Transfer in *Rb. sphaeroides* and *Rb. capsulatus* Reaction Centers, *Journal of Physical Chemistry B.*, 2003, 106: 1799-1808.

(Continued)

*Primary Examiner* — Rosalynd Keys
*Assistant Examiner* — Jennifer C Sawyer
(74) *Attorney, Agent, or Firm* — Joseph T. Leone, Esq.; DeWitt Ross & Stevens S.C.

(57) ABSTRACT

Disclosed are compounds and methods for manipulating proteins in general and membrane proteins in particular. The compounds can be prepared from cholic acid, deoxycholic acid, lithocholic acid, or derivatives thereof. The compounds typically possess critical micelle concentrations lower than those of known detergents such as CHAPS and CHAPSO. Accordingly, lower amounts of the compounds are required for effective solubilization of membrane proteins. The compounds can be used aid the solubilization, isolation, purification, stabilization, crystallization, and/or structural determination of membrane proteins.

25 Claims, 11 Drawing Sheets

(56) References Cited

OTHER PUBLICATIONS

Kirmaier et al., Detergent Effects on primary charge separation in wild-type and mutant Rhodobacter capsulatus reaction centers, *Chemical Physics.*, 2003, 294: 305-318.

Laible et al., Protein Modifications Affecting Triplet Energy Transfer in Bacterial Photosynthetic Reaction Centers, *Biophysical Journal*, 1998, 74: 2623-2637.

Laible et al., Quinone Reduction via secondary B-Branch Electron Transfer in Mutant Bacterial Reaction Centers, *Biochemistry* 2003, 42, 1718-1730.

March, J., *Advanced Organic Chemistry, Reactions, Mechanisms and Structure*, (5th Ed.), McGraw Hill: New York, © 1992, ISBN 978-0471601807 (Book).

McGregor et al., Lipopeptide detergents designed for the structural study of membrane proteins, *Nat. Biotechnol.* 2003, 21, 171-176.

Nugebauer, J. M., Detergents: An Overview, *Methods in Enzymology*, 1990, 182:239-253.

Pokkuluri et al., The Structure of a Mutant Photosynthetic Reaction Center Shows Unexpected Changes in Main Chain Orientations and Quinone Position, *Biochemistry*, 2002, 41: 5998-6007.

Popot et al., Amphipols From A to Z, *Annu. Rev. Biophys.* 2011, 40, 379-408.

Prive, Detergents for the stabilization and crystallization of Membrane proteins, *Methods* 2007, 41, 388-397.

Selao et al., Identification of Chromatophore Membrane Protein Complexes Formed under Different Nitrogen Availability Conditions in *Rhodospirillum rubrum*, *J. Proteome Res.* 2011, 10, 2703-2714.

Serrano-Vega et al., Conformational Thermostabilization of the $\beta$1-adrenergic receptor in a detergent-resistant form, *Proc. Natl. Acad. Sci. U. S. A.* 2008, 105, 877-882.

Wang et al., Comparative study of reaction centers from purple photosynthetic bacteria: Isolation and optical spectroscopy, *Photosynthesis Research*, 1994, 42: 203-215.

Yu et al., An improved tripod amphiphile for membrane protein solubilization, *Protein Sci.* 2000, 9, 2518.

Zhang et al., Designing Facial Amphiphiles for the Stabilization of Integral Membrane Proteins, *Angew. Chem. Int. Ed.* 2007, 46, 7023-7025.

Zhang et al., New amphiphiles for membrane protein structural biology, *Methods* 2011, 55, 318-323.

Zhao et al., Designer short peptide surfactants stabilize G protein-coupled receptor bovine rhodopsin, *Proc. Natl. Acad. Sci. U.S.A.* 2006, 103, 17707-17712.

Regarding the spectrum
of Purified Protein

Is the value at 875 nm or  ——No→  LEVEL 0 DETERGENT
760 nm greater than 0.1?

Is $A_{875}/A_{760}$ greater than 7  ——Yes→  LEVEL 1 DETERGENT
and $A_{800}/A_{760}$ greater than 2?

Is $A_{875}/A_{760}$ less than 7  ——Yes→  LEVEL 2 DETERGENT
and greater than 3.5?

Is $A_{875}/A_{760}$ less than 3.5  ——Yes→  LEVEL 3 DETERGENT
and greater than 1?

Is $1 \geq A_{875}/A_{760} > 0.2$
and is the longest wavelength  ——Yes→  LEVEL 4 DETERGENT
peak > 860 mn?

Is $1 \geq A_{875}/A_{760} > 0.2$
and is the longest wavelength  ——Yes→  LEVEL 5 DETERGENT
Peak < 860 mn?
                                    ↘ No
                                        LEVEL 6 DETERGENT

FIG. 8

CHOLATE AND DEOXYCHOLATE-BASED AMPHIPHILES FOR MEMBRANE PROTEIN MANIPULATION

CROSS-REFERENCE TO RELATED APPLICATIONS

Priority is hereby claimed to provisional application Ser. No. 61/910,574, filed Dec. 2, 2013, which is incorporated herein by reference.

FEDERAL FUNDING STATEMENT

This invention was made with government support under GM075913 awarded by the National Institutes of Health. The government has certain rights in the invention.

BACKGROUND OF THE INVENTION

Isolation and physical characterization of membrane proteins remains a central challenge in the biomolecular sciences. Isolating membrane proteins and obtaining their crystal structures is important to furthering an understanding of their function and role in metabolic pathways. Membrane proteins are difficult to manipulate and ultimately crystallize because these macromolecules are rarely soluble in simple aqueous buffers. The lack of efficient methods for isolating, purifying, and crystallizing membrane proteins represents a significant hindrance to fundamental and applied biological research because these proteins perform so many crucial functions in vivo.

Solubilizing membrane proteins for physical characterization and crystallization requires that the membrane protein be combined with a synthetic amphiphile, typically a detergent. The resulting crystal is generally a protein-detergent complex rather than solely the isolated protein. The detergent therefore plays an important role in determining whether high quality crystals will form. High quality crystals are essential for structural determination and characterization, such as by X-ray crystallography.

Determining the three-dimensional structure of membrane proteins has been successful only within the past two decades. Thus, the set of known membrane protein structures is far smaller than the set of known soluble protein structures. Synthetic amphiphiles are used to extract embedded proteins from the membranes in which they naturally occur and to maintain native protein conformation in the solubilized state. Physical characterization is often carried out with protein-amphiphile complexes. Such complexes are usually the basis for crystallization efforts. The ability to grow high quality crystals is typically the rate-limiting step in structure determination. Thus, synthetic amphiphiles that can aid crystal formation are crucial tools in this field.

In view of the limited detergents available for solubilizing and stabilizing membrane proteins, there exists a need in the field for alternative detergents with expanded and/or unique protein solubilizing and stabilizing properties. Thus, new amphiphiles for solubilizing and stabilizing membrane proteins are needed to aid fundamental and applied protein research. Preferably the amphiphiles could be synthesized from readily available starting materials and would solubilize membrane proteins at lower concentrations of the amphiphile than are needed for currently available detergents such as CHAPS (3-[(3-cholamidopropyl)-dimethylammonio]-1-propanesulfonate) and CHAPSO (3-[(3-cholamidopropyl)-dimethylammonio]-2-hydroxy-1-propanesulfonate).

SUMMARY

The invention provides new tools for membrane technology, including effective solubilizing agents and methods for solubilizing, isolating, and characterizing proteins in general and membrane proteins in particular. The solubilizing agents can include synthetic amphiphiles that exhibit favorable solubilization and stabilization properties in challenging biochemical systems such as, for example, lipid bilayers and photosynthetic superassemblies. Accordingly, novel compounds that are cholate-, deoxycholate-, and lithocholate-based amphiphiles (designated CAO, DCAO, and LCAO, respectively) and derivatives thereof, can be used for manipulating membrane proteins. The novel derivatives can be prepared from the readily available starting materials cholic acid, deoxycholic acid, and lithocholic acid, which are steroids found in bile:

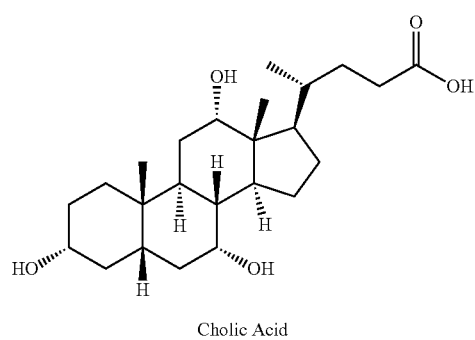

Cholic Acid

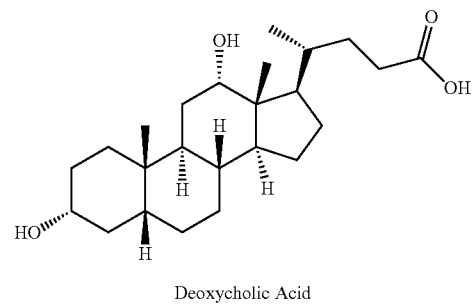

Deoxycholic Acid

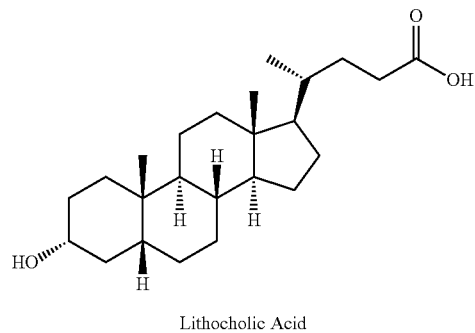

Lithocholic Acid

Specifically disclosed herein are compounds of Formula I:

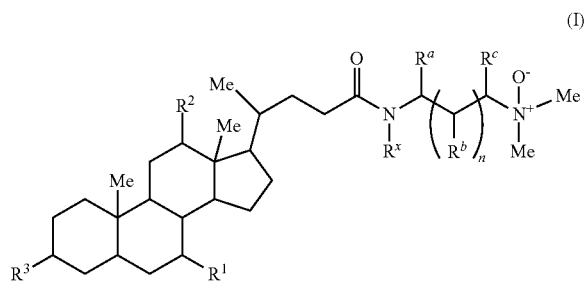

(I)

wherein $R^1$ is H or OH; $R^2$ is H or OH; $R^3$ is H or OH; $R^x$ is H or $C_1$-$C_6$-alkyl; "n" is 0, 1, 2, 3, or 4; and $R^a$, $R^b$, and $R^c$ are each independently H, OH, or $C_1$-$C_6$-alkyl.

In certain versions of the compounds, at least one of $R^2$, $R^3$, and $R^4$ is not H.

In certain versions of the compounds, each of $R^a$, $R^b$, and $R^c$ is H. Alternatively, the compounds also include those wherein at least one of $R^a$, $R^b$, and $R^c$ is not H, and also those wherein at least two of $R^a$, $R^b$, and $R^c$ are not H.

Compounds explicitly within the present disclosure include:

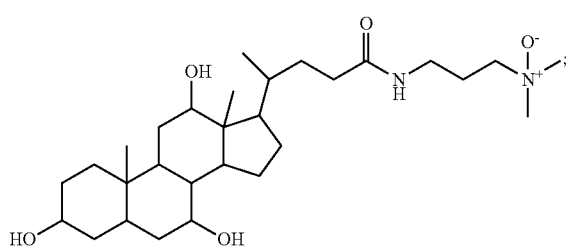

(CAO)

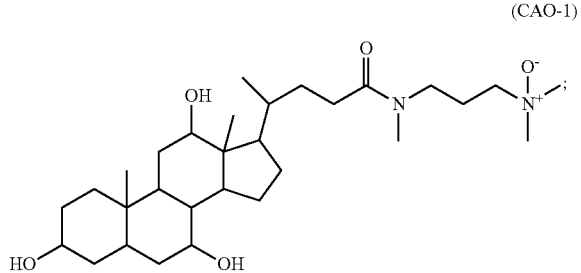

(CAO-1)

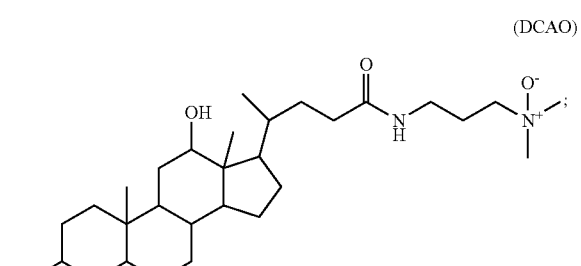

(DCAO)

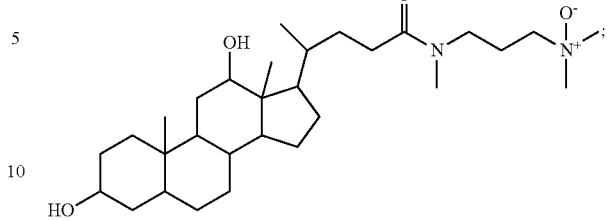

(DCAO-1)

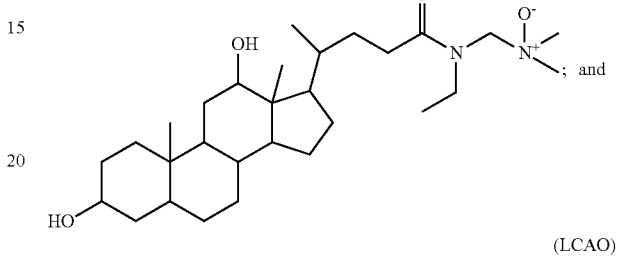

(DCAO-2)

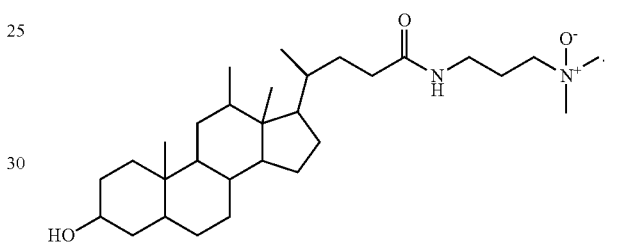

(LCAO)

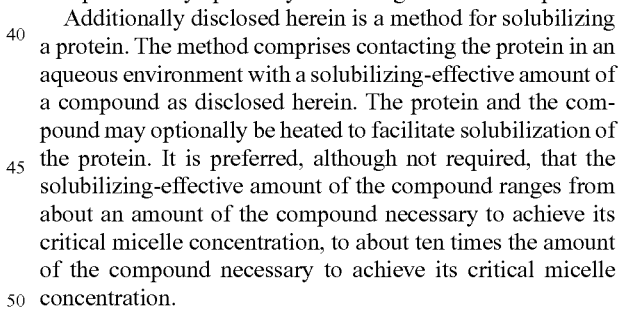

Also disclosed herein is a composition of matter comprising a compound as described herein, in combination with a protein in general, and/or a membrane protein in particular. The protein may optionally be an integral membrane protein.

Additionally disclosed herein is a method for solubilizing a protein. The method comprises contacting the protein in an aqueous environment with a solubilizing-effective amount of a compound as disclosed herein. The protein and the compound may optionally be heated to facilitate solubilization of the protein. It is preferred, although not required, that the solubilizing-effective amount of the compound ranges from about an amount of the compound necessary to achieve its critical micelle concentration, to about ten times the amount of the compound necessary to achieve its critical micelle concentration.

Also disclosed herein is a method for purifying a protein. The method comprises contacting a protein in an aqueous environment with a solubilizing-effective amount of a compound disclosed herein, thereby forming micelles comprising a plurality of the compounds surrounding the protein, and isolating the micelles.

The invention further provides compositions that include a compound described herein, such as one or more of the compounds described above, in combination with a membrane protein. In some embodiments, the membrane protein is an integral membrane protein.

The invention also provides methods for solubilizing a membrane protein. The methods can include contacting the protein in an aqueous environment with an effective amount of a compound described herein; and optionally heating the protein and the compound, to provide the solubilized protein encapsulated in a plurality of the compounds, such as micelles of the compound. The effective amount of the compound described herein can be about an amount of the compound necessary to achieve its critical micelle concentration, to about ten times, or to about twenty times, the amount of the compound necessary to achieve its critical micelle concentration.

The invention yet further provides methods of purifying a membrane protein. The methods can include contacting a protein in an aqueous environment with an effective amount of a compound described herein, thereby forming micelles comprising a plurality of the compounds surrounding the protein, and isolating the micelles, to provide the purified membrane protein encapsulated in micelles of the compound.

The invention additionally provides methods of stabilizing a membrane protein comprising contacting a protein in an aqueous environment with an effective amount of a compound described herein, thereby stabilizing the protein in its native tertiary conformation.

Under the specific experimental conditions evaluated, CAO did not perform as well as DCAO when evaluated for detergent solubilization properties. However, the amphiphile DCAO performed as well as or better than commercially available derivatives of cholic acid, such as CHAPS and CHAPSO, which are widely used as detergents for membrane isolation and solubilization. Moreover, the amount of DCAO required for solubilization (i.e., the critical micelle concentration (CMC) of DCAO) is approximately 8-fold lower than that of CHAPS or CHAPSO. Also, because of the low CMC, membrane proteins can be solubilized using lower concentrations of amphiphiles described herein compared to many currently used commercial detergents. Both DCAO and CAO, and their derivatives, can be readily prepared from commercially available starting materials. For example, DCAO can be synthesized in two steps from deoxycholic acid.

The invention therefore provides novel compounds and formulas, intermediates for the synthesis of the compounds and formulas, as well as methods of preparing the compounds, formulas, and compositions described herein. The invention also provides compounds that are useful as intermediates for the synthesis of other valuable compounds. The invention further provides methods of using the compounds, for example, to aid the solubilization, isolation, purification, stabilization, crystallization, and/or structural determination of membrane proteins. The compounds of the invention can be used alone, or in combination with lipids or known detergents. Other objects, features and advantages of the present invention will become apparent from the following description, claims and drawings.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. One skilled in the art, however, will understand that portions of the example or aspect may be used in combination with other examples or aspects of the invention.

DETAILED DESCRIPTION

Figures 1A, 1B:
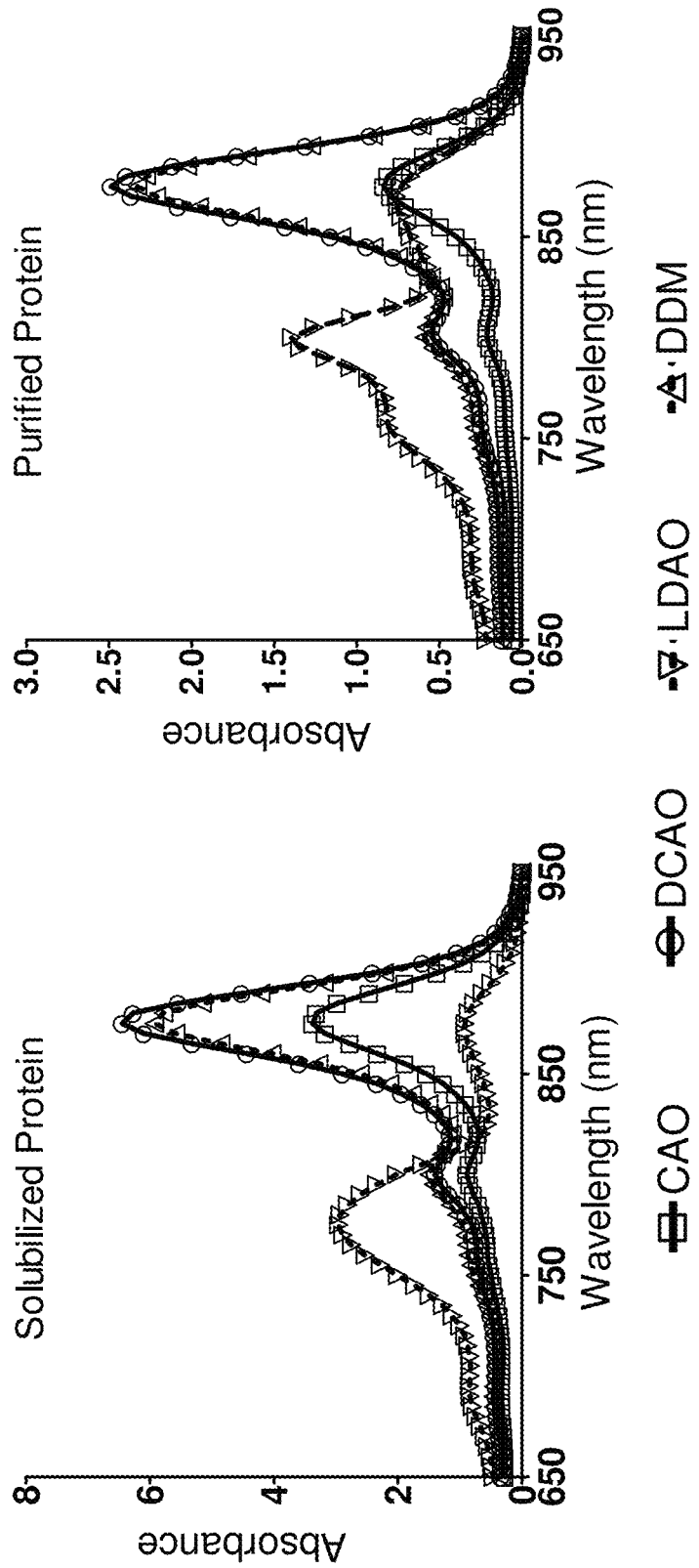
FIG. 1A is the absorbance spectra of *R. capsulatus* superassembly solubilized in two of the novel N-oxides described herein (CAO and DCAO) and two conventional detergents (DDM and LDAO).
FIG. 1B is the absorbance spectra of *R. capsulatus* superassembly purified in two of the novel N-oxides disclosed herein (CAO and DCAO) and two conventional detergents (DDM and LDAO). In both figures, the detergents were used at 2×CMC for CAO, 10×CMC for DCAO, and 50×CMC for DDM and LDAO due to the large variation of their CMC values. For purification of the protein, nickel-nitrilotriacetic acid (Ni-NTA) affinity column chromatography was performed and the protein complexes were eluted from the resin in the detergent concentration of 1×CMC.

Membrane proteins are hard to handle outside their native membranes mainly due to their inherent amphipathic characteristics. This necessitates using detergents to solubilize the membrane proteins to separate them from the membrane per se prior to structural and functional studies. Detergent micelles are excellent systems for encapsulating membrane proteins. The resulting protein-detergent complexes are subsequently solubilized and stabilized in an aqueous medium during subsequent protein manipulation.

Disclosed herein are novel N-oxide amphiphiles with hydrophobic moiety variations. The new amphiphiles were evaluated using a large, multi-subunit membrane protein assembly. Among these N-oxide amphiphiles, cholate- and deoxycholate-based agents containing three and two hydroxyl groups in the lipophilic regions, respectively, displayed significantly favorable behavior for membrane protein solubilization and/or stabilization. This result and others indicates that the identity and number of non-hydrocarbon groups, such as hydroxyl or ether groups, present in the hydrophobic region play a critical role in effective detergent properties. This structure-property relationship provides insight for designing novel agents for membrane protein research.

A large number of amphiphiles are needed for characterization and solubilization work because many alternatives must be tried for each membrane protein to identify the best match between detergent and target protein. Accordingly, the amphiphiles described herein provide additional resources to researchers for manipulating membrane proteins. For example, the amphiphiles disclosed herein can be used as reagents for protein solubilization and crystallization, especially for generally insoluble proteins. The amphiphiles can also be used as reagents for protein stabilization, so that the proteins can be analyzed by various ligand binding assays. For a continuously updated database of membrane-bound protein structures, each of which can be potentially suitably manipulated by the amphiphiles described herein, see: http://blanco.biomol.uci.edu/Membrane_Proteins_xtal.html.

Before the amphiphiles and methods are further described, it is noted that this disclosure is not limited to the particular methodology, protocols, materials, and reagents described herein, as these may vary. For example, various substituents and protecting groups can be added to compounds of Formula I to provide other compounds of the invention. When a chiral center is created by such substitution, each isomer is within the scope of the invention and is an intended part of the invention. It is also to be understood that the terminology used herein is for the purpose of describing particular embodiments only and is not intended to limit the scope of the invention, which is limited only by the appended claims.

DEFINITIONS

The following definitions are included to provide a clear and consistent understanding of the specification and claims. As used herein, the recited terms have the following meanings. All other terms and phrases used in this specification have their ordinary meanings as understood by one of skill in the art. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

The following abbreviations are used:
β-UDM=undecyl-β-D-maltoside. CAO=cholate-based amphiphiles. CHAPS=3-[(3-cholamidopropyl)-dimethylammonio]-1-propanesulfonate. CHAPSO=3-[(3-cholamidopropyl)-dimethylammonio]-2-hydroxy-1-propanesulfonate. CMC=critical micelle concentration. DCAO=deoxycholate-based amphiphiles. DDM=n-dodecyl-β-D-maltoside. DPA=dipod amphiphiles. IMP=integral membrane protein. LCAO=lithocholate-based amphiphiles. LDAO=lauryldimethylamine oxide. LHI=light harvesting complex I. OG=n-octyl-β-D-glucopyranoside. PDC=protein-detergent complex. RC=resilient reaction center complex. TPA=tripod amphiphiles.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to extract a membrane protein from a cell membrane, that is effective to solubilize a membrane protein, or that is effective to stabilize a membrane protein. Thus, an "effective amount" generally means an amount that provides the desired effect.

The phrase "treating a protein" with a compound, detergent, surfactant, or "agent" refers to contacting the protein with the agent (e.g., an amphiphile as described herein), and/or combining the protein with an effective amount of the agent under conditions that allow the agent to penetrate, integrate and/or disrupt a protein's current environment in order to solubilize, stabilize, isolate, and/or purify the protein. The conditions can be aqueous and additional reagents, such as buffers, salts, and the like, can be added. The treating can use a single type of agent, such as an amphiphile described herein, or the treating can employ a combination of agents, such as an amphiphile described herein in combination with one or more surfactants such as DDM, CHAPS, CHAPSO, and the like. Thus, a combination of reagents may be employed in the treatment. The protein may be, for example, in a lipid bilayer or substantially isolated in solution.

Detergent-solubilized membrane proteins are typically more thermolabile than their membrane-embedded forms, therefore stabilizing a protein is important for research and analysis. The phrase "stabilizing a protein" refers to treating a protein so that the protein thermostability improves, or so that the protein retains activity (e.g., of a particular receptor), or maintains a native confirmation, for example, when extracted from a membrane. Stabilizing a membrane protein with an amphiphile as described herein can be, for example, improving its $T_{50}$ value by about 5° C., about 10° C., about 15° C., about 20° C., or about 25° C., for example, compared to a standard detergent such as DDM. Increasing the stability of an isolated protein is important to allow researchers sufficient time to examine and characterize the protein.

Methods of the invention include treating a protein, for example, using such techniques as solubilization, isolation, purification, stabilization, crystallization, and/or structural determination. The methods can include standard laboratory techniques such as lysing a cell, precipitation, concentration, filtration, and/or fractionation.

Specific values listed below for radicals, substituents, and ranges, are for illustration only; they do not exclude other defined values or other values within defined ranges for radicals and substituents.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be a monovalent hydrocarbon radical, as described and exemplified above, or it can be a divalent hydrocarbon radical (i.e., an alkylene), according to the context of its usage.

The term "alkoxy" refers to the group alkyl-O—, where alkyl is as defined herein. Examples of alkoxy groups include, but are not limited to, methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted as described for alkyl groups.

The term "substituted" indicates that one or more hydrogen atoms on the group indicated in the expression using "substituted" is replaced with a "substituent". The number referred to by 'one or more' can be apparent from the moiety on which the substituents reside. For example, one or more can refer to, e.g., 1, 2, 3, 4, 5, or 6; in some embodiments 1, 2, or 3; and in other embodiments 1 or 2, and if the substituent is an oxo group, two hydrogen atoms are replace by the presence of the substituent. The substituent can be one of a selection of indicated groups, or it can be a suitable group recited below or known to those of skill in the art, provided that the substituted atom's normal valency is not exceeded, and that the substitution results in a stable compound. Suitable substituent groups include, e.g., alkyl, alkenyl (e.g., vinyl, or allyl), alkynyl, alkoxy, halo (e.g., F, Cl, Br, or I), haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, alkylcarbonyloxy, amino, alkylamino, dialkylamino, trifluoromethyl, trifluoromethoxy, acylamino, nitro, carboxy, carboxyalkyl, keto, phosphate, sulfate, and cyano, as well as the moieties illustrated in the schemes and Figures of this disclosure; or combinations thereof. A substituent can also be a protecting group, for example, a hydroxyl protecting group.

In some embodiments, one or more substituents above can be excluded from the group of potential values for substituents on the substituted group. The various R groups in the schemes and figures of this disclosure can be one or more of the substituents recited above, thus the listing of certain variables for such R groups (including $R^1$, $R^2$, $R^3$, etc.) are representative and not exhaustive, and can be supplemented with one or more of the substituents above.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the amphiphiles described herein may be protected. For example, protecting groups for —OH groups (whether hydroxyl, carboxylic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art.

A very large number of hydroxyl protecting groups and amide-forming groups and corresponding chemical cleavage reactions are described in *Greene's Protective Groups in Organic Synthesis*, 4th Edition, Peter G. M. Wuts and Theodora W. Greene, ISBN: 978-0-471-69754-1, © 2006, John Wiley & Sons, Inc., New York, N.Y. ("Greene", which is incorporated herein by reference in its entirety). In particular, see Chapter 1 (The Role of Protective Groups in Organic Synthesis), Chapter 2 (Protection for the Hydroxyl Group, Including 1,2- and 1,3-Diols), Chapter 4 (Protection for the Carbonyl Group), Chapter 5 (Protection for the Carboxyl Group), and Chapter 10 (Reactivities, Reagents, and Reactivity Charts).

A hydroxyl protecting group can be, for example, allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl ("TBS")) or any other group that can be introduced chemically onto a hydroxyl functionality and later selectively removed either by chemical or enzymatic methods in mild conditions compatible with the nature of the product.

The "Critical Micelle Concentration" (CMC) refers to the concentration of a detergent (e.g., an amphiphile as described herein) in an aqueous solution at which the detergent molecules self-assemble into micelles. Below the CMC, detergents are mostly monomeric; above the CMC, micelle concentration increases linearly with detergent concentration. The CMC is dependent upon many factors and is detergent-specific. The CMC of a detergent can be determined experimentally by measuring the solubilization of a water-insoluble dye or fluorophore while varying the concentration of detergent. A CMC may also be determined by measuring the diminution of the surface tension of an aqueous solution as a function of detergent concentration (CMCs determined by either method correlate with each other). The CMC is determined by extrapolating the plot of solubilization vs. concentration (or surface tension vs. concentration) in the two linear regions above and below the CMC. Where the two lines intersect is the CMC. The CMC can also be determined by the method of Nugebauer, J. M. (1990), *Methods in Enzymology*, 182:239-253.

Amphiphiles for Membrane Protein Manipulation:

Manipulation of membrane proteins remains a profound technical challenge. A variety of different amphiphiles are needed on the market, as different amphiphiles are useful for different target proteins, depending on the properties of the protein and the in vitro use proposed. The best amphiphile for any particular protein is difficult or impossible to predict, and requires empirical testing. Researchers most often cannot predict which amphiphile will be suitably effective for manipulating a particular membrane protein. Data acquired for the new amphiphiles shows that they are comparable or superior to known detergents for membrane protein manipulation. Therefore the new amphiphiles described herein provide additional valuable tools for the manipulation of membrane proteins.

A variety of known biochemical detergents are based on cholic acid (see Hjelmeland, *Methods in Enzymology*, Vol. 124; 1986, 135-164). Two commonly used detergents are CHAPS and CHAPSO. While CHAPS and CHAPSO have found widespread use, these amphiphiles have many limitations and they are not suitable for the solubilization and isolation of most membrane proteins.

The new detergents described herein have been evaluated with an *R. capsulatus* photosynthetic superassembly solubilization assay. The assay was previously used to evaluate CHAPS and CHAPSO, as well as numerous other commercial detergents. CAO did not perform as well as DCAO in the specific assays, but still displayed acceptable solubilization activity. The data obtained for DCAO substantially matched or exceeded the utility of CHAPS and CHAPSO in terms of solubilization. Moreover, the CMC of DCAO is approximately 8-fold lower than that of CHAPS or CHAPSO. Accordingly, less DCAO is required to provide similar membrane protein manipulation, which is important for successful crystallization and characterization.

It was found that functionalizing the cholate or deoxycholate carboxylic acid moiety with a specific polar head group provided highly active amphiphilic detergents that have surprisingly low CMCs. In some embodiments, the carboxylic acid moiety of the cholate structures was functionalized by amide bond formation between the acid and an amine terminating in a dimethyl-N-oxide group. The preparation and use of such amphiphiles is further described herein below.

Thus, disclosed herein are compounds and compositions that can include a plurality of amphiphilic compounds described herein and a membrane protein, such as an integral membrane protein. Such compositions can take the form of aggregates or micelles, formed from a plurality amphiphilic compounds as described herein, optionally in conjunction with one or more other surfactant compounds and/or micelle-forming compounds, where the plurality of compounds surround the membrane protein. The composition can optionally include a polypeptide, a protein, and/or one or more other types of biological molecules complexed with the amphiphilic compound.

Also disclosed herein are methods of solubilizing a membrane protein by contacting the membrane protein with a plurality of a compound described herein, in an aqueous solution, thereby forming a solubilized aggregation of the compounds and the membrane protein. Also disclosed are methods of stabilizing a membrane protein by contacting the membrane protein with a plurality of a compound described herein, in an aqueous solution, thereby forming an aggregation of the compounds and the membrane protein. Additionally disclosed herein are methods of extracting a protein from a lipid bilayer by contacting the lipid bilayer with a plurality of a compound described herein in an aqueous solution to form a mixture, optionally in the presence of a buffer or other detergent, thereby forming an aggregation of the compounds and the membrane protein extracted from the lipid bilayer. The aggregation can then be separated from the mixture to provide isolated and/or purified membrane protein.

Accordingly, the invention provides various methods for manipulating membrane proteins. For example, a method is provided for solubilizing a membrane protein by contacting the protein in an aqueous environment with an effective amount of a compound as described herein, and optionally heating the protein and the compound, to provide the solubilized protein encapsulated in micelles of the compound. The effective amount of the compound can be an amount of the compound necessary to achieve its critical micelle concentration, to about 10 times, about 100 times, about 1,000 times, or about 10,000 times, the amount of the compound necessary to achieve its critical micelle concentration. The method can also include employing a buffer, heat, a second amphiphile or detergent, or other reagents, in the aqueous environment to aid in the solubilization and stabilization of membrane proteins.

The invention also provides a method of purifying a membrane protein by contacting the protein in an aqueous environment with an effective amount of a compound as described herein, to form micelles comprising a plurality of the compounds surrounding the protein, and isolating the micelles, to provide the purified membrane protein encapsulated in micelles of the compound. Other techniques for using the amphiphilic compounds described herein include techniques for stabilizing, crystallizing, and/or characterizing a protein while in a detergent micelle made up of a compound described herein.

The invention has several advantages over previous membrane manipulation technologies. For example, the amphiphiles described herein can lack any aromatic groups, therefore they are highly suitable for "optical" characterization methods such as UV absorbance spectroscopy and UV circular dichroism, when characterizing a protein solubilized by such amphiphiles.

Other uses of the amphiphiles described herein include their use as amphiphilic additions in crystallization trials, components of detergent mixtures, stabilizing factors in functional assays, detergents in exchange schemes, solubilization agents in cell-free expression reactions, as well as their use for separation on polyacrylamide gels using native protocols to maintain native states, for use in sample buffers on membrane fractions used to solubilize membrane proteins and to prepare proteins for separation on gels, and for use with "BUG-BUSTER"®-brand Protein Extraction Reagent formulations designed to break open cells and survey proteins present, for example, without using sonication and/or lysozyme treatment and osmotic shock, such as with eukaryotic cell pellets that are relatively fragile and easily disrupted. ("BUG-BUSTER" is a registered trademark of Merck, KGaA, Darmstadt, Germany.)

The amphiphiles described herein can also aid the formation of well-ordered crystals of membrane protein-amphiphile complexes. When a membrane protein-amphiphile complex crystallizes, amphiphiles can be included within the crystal lattice or in other embodiments, excluded from the crystal lattice. The amphiphiles can contribute to the ordering of proteins within the lattice when crystals are formed, thereby aiding the stability of growing membrane protein crystals.

The amphiphiles can stabilize membrane proteins, such as integral membrane proteins, in native conformations, for example, for protein structural characterization. The amphiphiles can extract proteins from lipid bilayers and stabilize the protein comparably or more effectively than conventional biological detergents. The amphiphiles can further be used for membrane protein research including isolation, stabilization, analysis by solution NMR, and biochemical and biophysical assay development.

The invention can therefore be directed to amphiphiles that can enhance the ability of a composition to solubilize and crystallize membrane-bound proteins into well-order crystals. The amphiphiles described herein can be used in any application where conventional detergents are used. For instance, the amphiphiles can be used to lyse cellular membranes. The amphiphiles can also form micelles in an aqueous solution.

They can therefore be used to solubilize hydrophobic compounds for dispersion into aqueous solution. More specifically, the amphiphiles are useful for solubilizing membrane proteins, such as integral membrane proteins.

The amphiphiles described herein can be used alone, or in combination with other biological detergents, such as DDM, undecyl-β-D-maltoside (β-UDM), 3-[(3-cholamidopropyl)-dimethylammonio]-1-propanesulfonate (CHAPS), 3-[(3-cholamidopropyl)-dimethylammonio]-2-hydroxy-1-propanesulfonate (CHAPSO), lauryldimethylamine oxide (LDAO), octyl-glucoside (OG) or other detergents described by Hjelmeland in *Methods of Enzymology*, Vol. 124, page 135-164, which is incorporated herein by reference. For example, a particular detergent may to too harsh to suitable solubilize a membrane protein in its native conformation, however a combination of an amphiphiles described herein and a commercial biological detergents can provide reduced severity, thereby allowing the protein to be maintained in its native conformation while maintaining solubility.

N-Oxide Amphiphiles for Membrane Protein Manipulation:

Integral membrane proteins (IMPs) reside in lipid bilayer and play crucial roles in many cellular processes represented by signal transduction and material transfer between the inside of a cell and its environment. The fact that more than membrane proteins are targets for many pharmaceutical agents in development underlines the importance of these bio-macromolecules' roles in physiological states of cells. Currently, more than 80,000 protein structures are available from the protein data bank (PDB). The set of membrane proteins with known structures, however, constitutes only about 0.5% of the total number of known protein structures, indicating the notorious difficulty in membrane protein structural determination. This discrepancy between membrane proteins and soluble counterparts results from three major barriers associated with membrane-bound proteins.

First, membrane proteins generally have very low natural abundance compared to soluble proteins. Thus, it is difficult to obtain a sufficient amount of membrane protein for structural study. Second, these bio-macromolecules are highly unstable once removed from a lipid bilayer. In order to obtain high resolution crystal structures, membrane proteins must be first extracted from their native membranes using amphipathic compounds (e.g., detergents) and retain their native structures during subsequent processes such as purification and crystallization. Because a detergent micelle environment is significantly different than the environment of a protein's native membrane, detergent-solubilized membrane proteins tend to denature and aggregate, leading to loss of their function in an aqueous medium. Third, membrane proteins solubilized with detergents, called protein-detergent complexes (PDCs), have high conformational flexibility originating from both the detergent molecules as well as the structure of the membrane proteins.

Conventional detergents typically include a flexible alkyl chain and a hydrophilic group such as an N-oxide, glucose, or maltose, as exemplified by lauryldimethylamine-N-oxide (LDAO), n-octyl-β-D-glucopyranoside (OG) and n-dodecyl-β-D-maltoside (DDM). Membrane proteins are evolved to utilize a flexible loop to connect between two α-helixes or two domains. The multiple loops endow a membrane protein with high conformational flexibility for proper function. However, the highly flexible characteristic of PDCs would play an unfavorable role in generating protein crystal lattices, the formation of which require a highly ordered state (Chae, Laible, and Gellman; *Mol. BioSyst.* 2010, 6, 86-94). An ideal detergent should possess the variety of properties needed to overcome these three barriers.

The design of effective detergent molecules is very challenging because multiple properties need to be possessed by a single detergent structure. More than 100 conventional detergents are commercially available but only a few are widely used for membrane protein research. Membrane proteins solubilized in even the most popular detergents are vulnerable to denaturation and aggregation (Serrano-Vega et al., *Proc. Natl. Acad. Sci. U.S.A.* 2008, 105, 877-882). Thus, it is of great interest to develop novel classes of amphiphiles with enhanced properties in terms of membrane protein solubilization and stabilization.

Over the past a few decades, several types of amphiphiles have been devised to facilitate membrane protein study. Examples include:

tripod amphiphiles (TPAs) by Gellman and coworkers, *Angew. Chem. Int. Ed.* 2000, 39, 758; *ChemBioChem* 2008, 9, 1706;

hemifluorinated surfactants (HFSs), Breyton et al., *FEBS Lett.* 2004, 564, 312; Popot et al., *Annu. Rev. Biophys.* 2011, 40, 379; Cho, Byrne, and Chae, *ChemBioChem* 2013, 14, 452;

peptide-based amphipathic oligomers, McGregor et al., *Nat. Biotechnol.* 2003, 21, 171; Zhao et al., *Proc. Natl. Acad. Sci. U.S.A.* 2006, 103, 17707;

cholate or cholesterol-based amphiphiles, Zhang et al., *Angew. Chem. Int. Ed.* 2007, 46, 7023; Chae et al., *J. Am. Chem. Soc.* 2010, 132, 16750; Howell et al., *Biochemistry* 2010, 49, 9572; and rigid hydrophobic group-bearing amphiphiles, Chae et al., *Chem.-Eur. J.* 2012, 18, 9485; Hovers et al., *Mol. Membr. Biol.* 2011, 28, 170.

Amphiphilic polymers such as amphipols (Apols), nanodiscs (NDs) and lipodisqs are innovative approaches to overcome the limitation of amphiphiles with low molecular weights. Recently, maltose-neopentyl glycol (MNG) (Cho, Byrne, and Chae, *ChemBioChem* 2013, 14, 452; Chae et al., *Nat. Methods* 2010, 7, 1003; Selao et al., *J. Proteome Res.* 2011, 10, 2703) and glucose-neopentyl glycol (GNG) amphiphiles (Chae et al., *Chem. Comm.* 2013, 49, 2287) were shown to be extremely promising in providing high resolution crystal structures of more than 10 membrane proteins including several G-protein coupled receptors (GPCRs), culminating important roles of new detergents in membrane protein structure study. Very recently, the carbohydrate versions of Triton X-100, designated CGT, proved to be effective at membrane protein solubilization and stabilization (Chae et al., *Mol. BioSyst.* 2013, 9, 626). Despite a wealth of studies on this large number of conventional detergents and novel agents, information on detergent structure-property relationships is seriously limited.

The importance of non-hydrocarbon groups in the hydrophobic portion of various N-oxide amphiphiles was evaluated and was found to have a significant impact on the properties of the amphiphile, as described herein. Elucidating these relevant relationships will have a greater impact on membrane protein research than the development of a single well-behaving agent because structure-property relationships will provide useful guidelines in future development of novel classes of amphiphiles, as well as insight into selecting detergent candidates suited for a specific 'target' membrane protein.

The invention provides new cholate-based amphiphiles for the manipulation of membrane proteins. For example, the invention provides a composition comprising a plurality of compounds as described above and an isolated membrane protein. The composition can include micelles that include the compounds described herein encapsulating the isolated membrane protein, optionally in combination with other compounds, amphiphiles, or surfactants in the micelle structure. The micelle can optionally include one or more drugs, therapeutic molecules, bioactive molecules, polypeptides, proteins, genes, or a combination thereof, within the micelle. In some embodiments, the molecule within the micelle is a polypeptide or a protein.

The invention also provides methods of solubilizing or stabilizing a membrane protein comprising contacting a membrane protein with an effective amount of a plurality of compounds described herein, in an aqueous solution. The methods can and optionally include heating the protein and the compounds, thereby forming a solubilized or stabilized aggregation or micelle of the compounds and the membrane protein. The invention further provides methods of extracting a protein from a lipid bilayer comprising contacting the lipid bilayer with an effective amount a plurality of compounds described herein in an aqueous solution or suspension to form a mixture, optionally in the presence of a buffer, thereby forming an aggregation or micelle of the compounds and the membrane protein that has been extracted from the lipid bilayer. The aggregates and/or micelles can then be separated from the mixture to provide the isolated proteins. The compounds described herein can be particularly valuable for stabilizing proteins in a functional form such that the protein can be analyzed by various assays, such as a ligand binding assay.

Typical detergents such as DDM, OG and LDAO have simple alkyl chains as the lipophilic groups. In the presence of a membrane protein, these amphiphiles associate with one another to cover the hydrophobic surfaces of the protein, resulting in protein-detergent complexes (PDCs). The overall architectures of the amphiphiles introduced herein are neither facially amphiphilic nor polymeric. Consequently, the new agents are anticipated to associate with membrane protein similarly to classical detergents. Since, however, the lipophilic groups of the new cholate-derived amphiphiles described herein are rigid and flat, these molecules will display a stronger tendency to associate with complementary protein surfaces than do conventional detergents, and this tendency underlies the favorable solubilization and stabilization properties documented herein.

Solubilization Assays:

Light harvesting (LH) and reaction center (RC) complexes from photosynthetic bacteria (for example, R. capsulatus) are highly suitable for use in solubilization assays. These complexes, normally embedded in the bacterial membrane, are highly pigmented and several outcomes from an assay are possible, including no degradation, partial degradation or complete degradation upon solubilization, or no solubilization. Thus, graded comparative evaluations could be obtained for a set of candidates such as DCAO and CAO. In the engineered strain of R. capsulatus employed, the photosynthetic unit was comprised of a very labile LHI complex and a more resilient RC complex. An ideal amphiphile will extract the intact LHI-RC superassembly from a bacterial membrane preparation and maintain the natural interactions among the components. Amphiphiles with a more disruptive effect will dissociate and denature LHI, leaving only intact RC, and even harsher amphiphiles will cause RC degradation. Each of these various outcomes can be assessed unambiguously via optical spectroscopy.

Compound Characterization and Methods:

The Critical Micelle Concentrations (CMCs) of compounds of the invention can be determined by standard techniques known to those of skill in the art. For example, CMCs of CAO and DCAO can be determined by monitoring uptake of a fluorescent dye (e.g., a dye such as 1,6-diphenylhexatriene) with increasing detergent concentration, monitored by fluorescence spectroscopy.

In some embodiments, the critical micelle concentration (CMC) of a compound described herein in water is about 0.5 mM to about 20 mM. In various embodiments, the CMC can be about 0.5 mM to about 15 mM, about 0.5 mM to about 10 mM, about 0.5 mM to about 2 mM, about 5 mM to about 10 mM, or about 7 mM to about 9 mM.

When using the compounds of the invention for solubilization, isolation, purification, stabilization, crystallization, and/or structural determination of membrane proteins, they can be used alone, or in combination with known detergents, such as CHAPS and/or CHAPSO, or other detergents, such as those described in U.S. Pat. No. 6,172,262 (McQuade et al.); and U.S. Pat. No. 8,263,754 (Gellman et al.) and by Hjelmeland in *Methods of Enzymology*, Vol. 124, page 135-164, which are incorporated herein by reference.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Amphiphile Synthesis

A. General Procedures for Solvolysis Reactions.

This procedure was followed the literature method (Yu et al., *Protein Sci.* 2000, 9, 2518) with slight modification, as follows. A saturated dinitrile derivative (10 mmol) was mixed with ethylene glycol (50 mL) and potassium hydroxide (50 mmol). The mixture was refluxed for 3 days at 200° C. The reaction mixture was then cooled to room temperature and diluted with 50 mL of water. The solution was poured into ice-cold aqueous 6 M HCl (100 mL) and the resulting solution was extracted with ether (3×50 mL). The organic layers were combined, dried with $Na_2SO_4$, and concentrated by rotary evaporation. Flash column chromatography (EtOAc/hexane) affords a carboxylic acid derivative as a white solid.

B. General Procedures for Amide Coupling and Oxidation Reactions.

Carboxylic acid (5.0 mmol), dimethyamine derivative (5.5 mmol), 1-hydroxy-benzotriazole monohydrate (HOBt) (0.79 g, 5.9 mmol) was dissolved in anhydrous DMF (30 mL). 1-(3-(dimethylamino)propyl)-3-ethylcarbodiimide hydrochloride (EDC•HCl) (1.2 g, 5.9 mmol) was added in small portions at 0° C. and the resulting solution was stirred at room temperature for 20 h. The solution was taken up with ether (3×100 mL) and was washed successively with a 1 M aqueous $NaHCO_3$ solution (100 mL), a 0.1 M aqueous HCl solution (100 mL), and brine (2×100 mL). Then the organic layer was dried with $Na_2SO_4$ and the solvents were removed by rotary evaporation. The resulting residue was dissolved in chloroform (30 mL). The solution was cooled to −10° C., m-chloroperoxybenzoic acid (mCPBA) (2.0 g, 11.6 mmol) was added. The reaction was stirred for 4 h, and the reaction mixture was evaporated at room temperature. The residue was purified by alumina column chromatography (MeOH/$CH_2Cl_2$) and recrystallized in ether/$CH_2Cl_2$ to provide N-oxide amphiphile as a white solid.

Scheme 1-1.
Preparation of DPA-1 and Conditions for Preparation of Related Compounds.

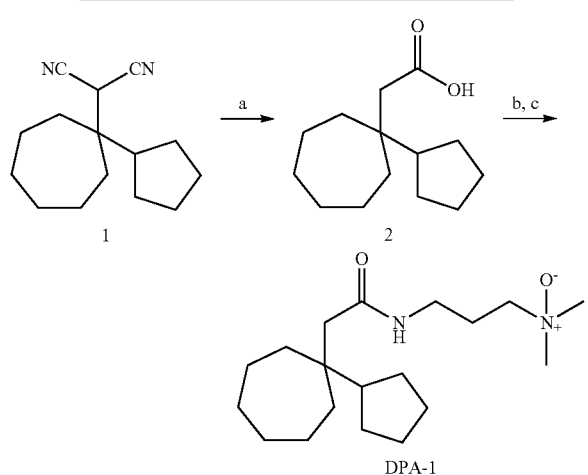

(a) KOH, ethylene glycol, 200° C.
(b) 3-(dimethylamino)-1-propylamine, EDC•HCl, DMF, room temperature.
(c) m-CPBA, CHCl$_3$, -10° C.

2-(1-cyclopentylcycloheptyl)malononitrile (1) was prepared according to a literature method (Chae et al., *J. Am. Chem. Soc.* 2010, 132, 1953). $^1$H NMR (300 MHz, CDCl$_3$): δ 3.78 (s, 1H), 2.13-1.97 (m, 1H), 1.95-1.70 (m, 4H), 1.70-1.30 (m, 16H); $^{13}$C NMR (75 MHz, CDCl$_3$): δ 113.1, 50.3, 45.5, 35.3, 33.0, 30.7, 27.7, 24.6, 24.0; HRMS (ESI): calcd. for C$_{15}$H$_{22}$N$_2$ [M–H]$^+$ 229.1710. found 229.1706.

2-(1-cyclopentylcycloheptyl)acetic acid (2) was prepared in 88% yield according to the general protocol for solvolysis reaction. $^1$H NMR (300 MHz, CDCl$_3$): δ 2.26 (s, 2H), 2.12-1.92 (m, 1H), 1.72-1.38 (m, 16H), 1.36-1.18 (m, 2H); $^{13}$C NMR (75 MHz, CDCl$_3$): δ 179.9, 49.7, 42.9, 41.5, 36.9, 30.9, 27.1, 25.5, 23.8; HRMS (ESI): calcd. for C$_{14}$H$_{24}$O$_2$ [M–H]$^+$ 223.1703. found 223.1711.

3-(2-(1-cyclopentylcycloheptyl)acetamido)-N,N-dimethylpropan-1-amine oxide (DPA-1) was prepared in 90% yield according to the general protocol for amide coupling and oxidation reactions. $^1$H NMR (300 MHz, CDCl$_3$): δ 8.18 (br s, 1H), 3.42-3.32 (m, 4H), 3.21 (s, 6H), 2.20-1.98 (m, 5H), 1.76-1.36 (m, 16H), 1.18-1.38 (m, 2H); $^{13}$C NMR (75 MHz, CDCl$_3$): δ 173.2, 69.6, 59.5, 49.5, 44.8, 41.1, 37.5, 37.1, 27.0, 25.5, 23.9, 23.8; HRMS (ESI): calcd. for C$_{19}$H$_{36}$N$_2$O$_2$ [M+H]$^+$ 325.2850. found 325.2839.

DPA-2 and DPA-3 were prepared according to the reported procedure (Chae et al., *J. Am. Chem. Soc.* 2010, 132, 1953).

Dipod amphiphile (DPA-2). $^1$H NMR (300 MHz, CDCl$_3$): 8.93 (br s, 1H), 7.30-7.20 (m, 8H), 7.18-7.12 (m, 2H), 4.64 (t, J=8.3 Hz, 1H), 3.24 (quin, J=6.1 Hz, 2H), 3.06 (t, J=6.4 Hz, 2H), 3.01 (s, 6H), 2.90 (d, J=7.9 Hz, 2H), 1.87 (quin, J=6.0 Hz, 2H); $^{13}$C NMR (75 MHz, CDCl$_3$): 171.3, 144.3, 128.5, 128.1, 126.3, 69.5, 59.5, 47.4, 43.1, 37.5, 24.0; HRMS (ESI): calcd. for C$_{20}$H$_{26}$N$_2$O$_2$[M+H]$^+$ 327.2068. found 327.2055.

Dipod amphiphile (DPA-3). $^1$H NMR (300 MHz, CDCl$_3$): 8.19 (s, 1H), 3.40-3.32 (m, 4H), 3.21 (s, 6H), 2.18-2.04 (m, 4H), 1.78-1.56 (m, 11H), 1.46-1.32 (m, 6H), 1.30-0.92 (m, 10H); $^{13}$C NMR (75 MHz, CDCl$_3$): 174.5, 69.8, 59.7, 45.2, 39.7, 37.7, 36.1, 31.9, 29.8, 27.2, 27.0, 26.9, 24.1; HRMS (ESI): calcd. for C$_{20}$H$_{38}$N$_2$O$_2$ [M+H]$^+$ 339.3007. found 339.2995.

SCHEME 1-2

Preparation of Cholate-Based Amphiphiles.

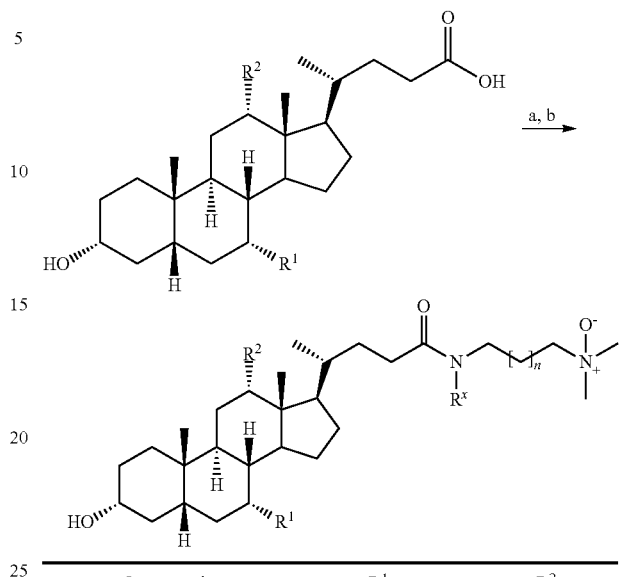

| Compound | R$^1$ | R$^2$ | | |
|---|---|---|---|---|
| CA | OH | OH | | |
| CA | OH | OH | | |
| DCA | H | OH | | |
| DCA | H | OH | | |
| DCA | H | OH | | |
| LCA | H | H | | |

| Compound | R$^1$ | R$^2$ | R$^x$ | n |
|---|---|---|---|---|
| CAO | OH | OH | H | 1 |
| CAO-1 | OH | OH | Me | 1 |
| DCAO | H | OH | H | 1 |
| DCAO-1 | H | OH | Me | 1 |
| DCAO-2 | H | OH | Et | 0 |
| LCAO | H | H | H | 1 |

(a) 3-(dimethylamino)-1-propylamine, EDC•HCl, HOBt, DMF, room temperature;
(b) (b) m-CPBA, CHCl$_3$, –10° C.

CAO was prepared in 91% yield according to the general protocol for amide coupling and oxidation reactions. $^1$H NMR (300 MHz, CDCl$_3$): δ 8.04 (s, 1H), 5.10 (s, 1H), 4.86 (s, 1H), 4.25 (s, 1H), 4.09 (s, 1H), 3.91 (s, 1H), 3.76 (s, 1H), 3.61-3.27 (m, 2H), 3.22 (s, 3H), 3.17 (s, 3H), 2.38-2.18 (s, 3H), 2.18-1.93 (m, 4H), 1.93-1.78 (m, 3H), 1.78-1.57 (m, 6H), 1.57-1.42 (m, 5H), 1.42-1.29 (m, 1H), 1.29-1.14 (m, 1H), 1.14-0.76 (m, 8H), 0.66 (s, 3H); $^{13}$C NMR (75 MHz, CDCl$_3$): δ 174.9, 77.4, 76.8, 73.2, 71.7, 68.5, 59.7, 58.4, 46.7, 46.1, 41.8, 41.7, 39.9, 39.7, 36.7, 35.8, 35.7, 35.3, 35.0, 32.6, 31.8, 30.8, 28.3, 28.0, 26.3, 23.6, 22.5, 17.8, 12.5; HRMS (ESI): calcd. for C$_{29}$H$_{52}$N$_2$O$_5$ [M+H]$^+$ 509.3949. found 509.3957.

DCAO was prepared in 89% yield according to the general protocol for amide coupling and oxidation reactions. $^1$H NMR (300 MHz, CDCl$_3$+5% CD$_3$OD): 3.9 (s, 1H), 3.50 (s, 8H), 3.35-3.20 (m, 4H), 3.15 (s, 6H), 2.33-2.17 (m, 1H), 2.16-1.96 (m, 3H), 1.93-1.68 (m, 7H), 1.68-1.32 (m, 11H), 1.32-1.16 (m, 2H), 1.16-0.94 (m, 5H), 0.91 (s, 3H), 0.68 (s, 3H); $^{13}$C NMR (75 MHz, CDCl$_3$+5% CD$_3$OD): δ 175.5, 73.1, 71.5, 58.3, 58.2, 46.7, 46.5, 42.2, 36.4, 36.2, 36.0, 35.5, 35.4, 34.2, 33.6, 33.0, 31.7, 30.0, 28.6, 27.6, 27.2, 26.3, 23.8, 23.4, 23.1, 17.2, 12.7; HRMS (ESI): calcd. for C$_{29}$H$_{52}$N$_2$O$_4$ [M+H]$^+$ 493.3922. found 493.3932.

LCAO was prepared in 85% yield according to the general protocol for amide coupling and oxidation reactions. $^1$H NMR (300 MHz, CDCl$_3$): δ 8.13 (s, 1H), 3.68-3.54 (m, 1H), 3.43-3.30 (m, 4H), 3.20 (s, 6H), 2.34-2.20 (m, 1H), 2.20-2.01 (m, 3H), 2.00-1.71 (m, 5H), 1.71-1.46 (m, 3H), 1.46-0.97 (m, 17H), 0.97-0.87 (m, 7H), 0.63 (s, 3H); $^{13}$C NMR (75 MHz, CDCl$_3$): δ 174.5, 77.4, 71.6, 69.1, 59.7, 59.5, 56.7, 56.5, 43.0, 42.3, 40.6, 40.4, 37.3, 36.9, 36.1, 35.8, 35.6, 34.8, 33.8, 33.2, 30.8, 28.5, 27.4, 26.7, 24.4, 23.6, 21.0, 18.7, 12.3; HRMS (ESI): calcd. for C$_{29}$H$_{52}$N$_2$O$_3$ [M+H]$^+$ 477.3871. found 477.3860.

CAO-1 was prepared in 93% yield according to the general protocol for amide coupling and oxidation reactions. $^1$H NMR (300 MHz, CDCl$_3$): 4.13 (br s, 5H), 3.91 (s, 1H), 3.78 (s, 1H), 3.68-3.52 (m, 1H), 3.46-3.12 (m, 10H), 3.18 (s, 2H), 2.94 (s, 1H), 2.51-2.35 (m, 1H), 2.35-2.04 (m, 5H), 2.04-1.17 (m, 18H), 1.14-0.76 (m, 8H), 0.67 (s, 3H); $^{13}$C NMR (75 MHz, CDCl$_3$): δ 174.5, 73.2, 71.7, 68.3, 68.4, 59.0, 58.6, 46.6, 46.4, 45.2, 41.9, 41.6, 39.7, 36.0, 35.8, 35.1, 35.0, 31.1, 30.6, 30.0, 28.3, 28.0, 26.3, 23.6, 22.5, 22.0, 17.7, 12.6; HRMS (ESI): calcd. for C$_{30}$H$_{54}$N$_2$O$_5$ [M+H]$^+$ 523.4106. found 523.4094.

DCAO-1 was prepared in 90% yield according to the general protocol for amide coupling and oxidation reactions. $^1$H NMR (300 MHz, CDCl$_3$): 3.97 (s, 1H), 3.66-3.39 (m, 2H), 3.31-3.11 (m, 8H), 3.05 (s, 3H), 2.94 (s, 1H), 2.90 (br s, 3H), 2.45-2.31 (m, 1H), 2.30-2.08 (m, 3H), 1.96-1.67 (m, 7H), 1.67-1.31 (m, 12H), 1.31-1.18 (m, 2H), 1.18-0.94 (m, 5H), 0.90 (s, 3H), 0.68 (s, 3H); $^{13}$C NMR (75 MHz, CDCl$_3$): δ 174.3, 73.2, 71.6, 68.8, 59.2, 59.1, 48.5, 47.2, 46.7, 45.1, 42.3, 36.7, 36.2, 35.8, 35.5, 34.3, 33.8, 31.1, 30.7, 30.4, 28.9, 27.8, 27.3, 26.4, 23.9, 23.3, 21.9, 17.7, 12.9; HRMS (ESI): calcd. for C$_{30}$H$_{54}$N$_2$O$_4$ [M+H]$^+$ 507.4157. found 507.4139.

DCAO-2 was prepared in 89% yield according to the general protocol for amide coupling and oxidation reactions. $^1$H NMR (300 MHz, CDCl$_3$): 3.97 (s, 1H), 3.92-3.80 (m, 2H), 3.66-3.51 (s, 1H), 3.51-3.32 (m, 4H), 3.20 (s, 6H), 3.16 (br s, 2H), 2.48-2.30 (m, 1H), 2.29-2.14 (m, 1H), 1.93-1.66 (m, 6H), 1.66-1.32 (m, 11H), 1.32-1.18 (m, 4H), 1.18-0.94 (m, 6H), 0.90 (s, 3H), 0.68 (s, 3H); $^{13}$C NMR (75 MHz, CDCl$_3$): δ 174.4, 73.2, 71.5, 67.3, 59.7, 59.5, 48.4, 47.3, 46.7, 43.9, 42.3, 41.4, 36.7, 36.2, 35.5, 34.3, 33.8, 31.5, 30.7, 29.9, 28.9, 27.7, 27.3, 26.4, 23.9, 23.3, 17.7, 14.6, 12.9; HRMS (ESI): calcd. for C$_{30}$H$_{54}$N$_2$O$_4$ [M+H]$^+$ 507.4157. found 507.4146.

As one of skill in the art would readily recognize, amphiphiles with varying linker lengths (i.e., compounds with varying values for "n") can be prepared by forming an amide using the corresponding amine in place of 3-(dimethylamino)-1-propylamine. Examples include 2-(dimethylamino)-1-ethylamine, 4-(dimethylamino)-1-butylamine, 5-(dimethylamino)-1-pentylamine, and 6-(dimethylamino)-1-hexylamine. The amide where IV is methyl or ethyl can be formed by using the corresponding substituted amine, e.g. N-methyl-3-(dimethylamino)-1-propylamine, etc.

The synthetic transformations described above are well known in the art and are generally described by reference works such as J. March, *Advanced Organic Chemistry, Reactions, Mechanisms and Structure*, (5th Ed.), McGraw Hill: New York, © 1992, ISBN 978-0471601807; Greg T. Hermanson in *Bioconjugate Techniques* (Academic Press, San Diego, Calif. (1996)); and F. Carey and R. Sundberg, *Advanced Organic Chemistry, Part B: Reactions and Synthesis*, 5th Ed., Plenum: New York, © 2008, ISBN 978-0387683546; and references cited therein. Other useful synthetic techniques are described in U.S. Pat. No. 6,172,262 (McQuade et al.) and U.S. Patent Publication Nos. 2009/0270598 (Gellman et al.) and 2010/0311956 (Gellman et al.).

Example 2

N-Oxide Amphiphiles for Membrane Protein Manipulation

Detergents are most generally classified into three categories depending on the electronic structures of hydrophilic groups: ionic, zwitterionic and nonionic detergents. In the field of membrane protein research, non-ionic agents are generally preferred over ionic and zwitterionic detergents because they are typically superior with respect to membrane protein stabilization (Prive, *Methods* 2007, 41, 388-397; Zhang et al., *Methods* 2011, 55, 318-323). However, ionic and zwitterionic detergents are usually better than non-ionic agents in terms of membrane protein solubilization. Thus, it is generally accepted that any particular detergent that is highly effective at stabilization has compromised properties with respect to solubilization in membrane protein manipulation. For example, a strongly-solubilizing agent is known to be a poor stabilizing agent in membrane protein study (McGregor et al., *Nat. Biotechnol.* 2003, 21, 171-176). Accordingly, new agents are needed that possess a combination of both good membrane protein solubilizing and stabilizing properties.

Representative zwitterionic detergents with a flexible alkyl group are Anzergent 3-12, which displays a sulfobetaine head group, and LDAO, which provides an N-oxide head group (Scheme 2-1). Of these two amphiphiles, LDAO is more widely useful in membrane protein structural studies via x-ray crystallography and nuclear magnetic resonance (NMR) spectroscopy. The wide use of this agent may be attributed to its ability to form small protein-detergent complexes (PDCs). A small PDC size generally serves a favorable role in crystal formation by exposing the large hydrophilic surface area of membrane proteins. Hydrophilic-hydrophilic protein interactions are known to be strong driving forces of crystal lattice formation. Small PDC size is also a favorable attribute in NMR-based structural studies because of the reduced rotational correlation time of an incorporated protein.

Scheme 2-1. Representative zwitterionic detergents.

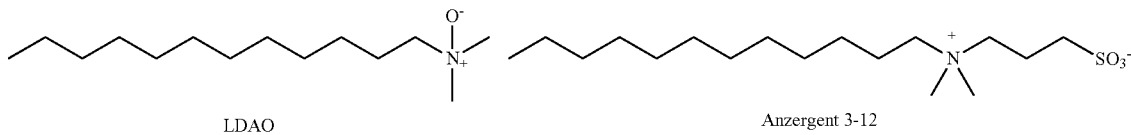

LDAO            Anzergent 3-12

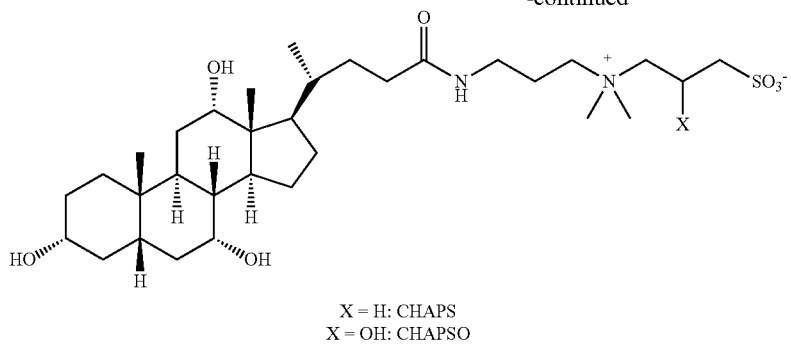

X = H: CHAPS
X = OH: CHAPSO

Because the N-oxide head group of CAOs is smaller than the sulfobetaine head group of CHAPS, the N-oxide agents disclosed and claimed herein will form small PDCs. This characteristic of N-oxide head group thus serves a favorable role in membrane protein crystallization.

On the other hand, cholate-based zwitterionic detergents with a sulfobetaine head group are known as mild detergents. Examples include 3-[(3-cholamindopropyl) dimethylammonio]-1-propanesulfonate (CHAPS) and 3-[(3-cholamidopropyl)dimethylammonio]-2-hydroxy-1-propanesulfonate (CHAPSO); (Scheme 2-1). These cholate-based zwitterionic detergents have interesting hydrophobic groups, i.e., a multi-fused ring system bearing three hydroxyl groups, at C3, C7 and C12, respectively. They are known to provide favorable properties for maintaining the native structure of fragile membrane proteins (protein stabilization).

Certain structural aspects of CHAPS and CHAPSO may provide a template for favorable membrane protein stabilization efficacy. Described herein is the design of certain N-oxide counterparts of these amphiphiles. The resulting agents possess a suite of combined characteristics, including the merit of a small head group and the mildness of cholate-based amphiphiles. In this disclosure, the preparation of N-oxide cholate-, deoxycholate-, and lithocholate-based amphiphiles is described. Dipod amphiphiles (DPAs) with two ring systems were also prepared, for comparison.

The new amphiphiles were evaluated for a large, multi-subunit membrane protein assembly, the *Rhodobacter* (R.) *capsulatus* photosynthetic superassembly. The results show that cholate- and deoxycholate-based N-oxide amphiphiles display favorable behaviors in superassembly manipulations compared to DPAs and conventional detergents (LDAO and DDM). More importantly, systematic variations in the amphiphile structures inform various structure-property relationships, which can serve as guidelines for the design of novel classes of amphiphiles.

Hydrophobic moiety variations of N-oxide amphiphiles are illustrated by several examples. Some of these examples include dipod amphiphiles (DPA-1, DPA-2 and DPA-3; Scheme 2-2), and cholate-, deoxycholate-, and lithocholate-based amphiphiles (designated CAO, DCAO and LCAO, respectively; Scheme 2-3).

Scheme 2-2. Chemical structures of newly-synthesized N-oxide amphiphiles with hydrophobic variations (DPA-1, DPA-2, DPA-3).

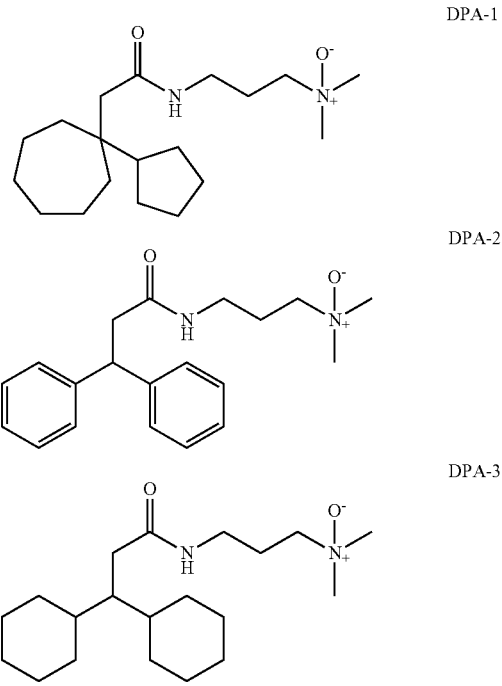

SCHEME 2-3

Chemical structures of newly-synthesized N-oxide amphiphiles with hydrophobic variations (CAO, CAO-1, DCAO, DCAO-1, DCAO-2, and LCAO).

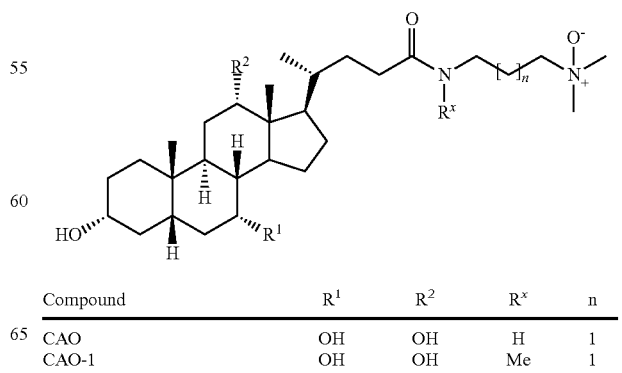

| Compound | $R^1$ | $R^2$ | $R^x$ | n |
|---|---|---|---|---|
| CAO | OH | OH | H | 1 |
| CAO-1 | OH | OH | Me | 1 |

SCHEME 2-3-continued

Chemical structures of newly-synthesized N-oxide amphiphiles with hydrophobic variations (CAO, CAO-1, DCAO, DCAO-1, DCAO-2, and LCAO).

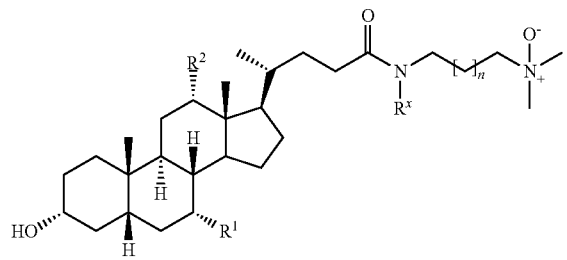

| Compound | $R^1$ | $R^2$ | $R^x$ | n |
|---|---|---|---|---|
| DCAO | H | OH | H | 1 |
| DCAO-1 | H | OH | Me | 1 |
| DCAO-2 | H | OH | Et | 0 |
| LCAO | H | H | H | 1 |

The DPAs share an N-oxide head group but vary in their hydrophobic groups; DPA-1 has cyclopentyl and cycloheptyl rings while DPA-2 and DPA-3 bear two benzene rings and cyclohexyl rings, respectively. On the other hand, CAO, DCAO and LCAO are unique in having a multi-fused ring-based hydrophobic group bearing different numbers of hydroxyl groups. To facilitate the synthesis of the multi-fused ring-bearing amphiphiles, three commercially available acid derivatives with various numbers of the hydroxyl groups were utilized: cholic acid, deoxycholic acid and lithocholic acid. All N-oxide amphiphiles were prepared in high synthetic yields (>85%) by straightforward synthetic methods such as amide coupling and oxidation with m-chloroperbenzoic acid (mCPBA) (see Example 1).

The amphiphiles prepared, except LDAO and DCAO, are water-soluble at up to 10 wt. %. LDAO was insoluble in water and thus was not exhaustively studied. DCAO was initially soluble, at approximately 1.0 wt. %, but tends to form a hydrogel over time at concentrations of greater than about 0.3 wt. %. Critical micelle concentration (CMC) values were estimated by using a hydrophobic fluorescent dye, diphenyhexatriene (DPH) (see Laible et al., Biochemistry 2003, 42, 1718-1730). Data for the new agents along with DDM, LDAO are provided in Table 2.1.

TABLE 2.1

Critical micelle concentrations (CMCs) and protein solubilization yields (SYs) for various synthetic amphiphiles and conventional detergents.

| | $MW^a$ | CMC (mM) | CMC (wt. %) | SY (%)$^b$ |
|---|---|---|---|---|
| DPA-1 | 324.5 | ~13 | ~0.24 | ~100 |
| DPA-2 | 326.4 | ~78 | ~2.5 | ~15 |
| DPA-3 | 338.5 | ~4.9 | ~0.17 | ~95 |
| CAO | 508.7 | ~8.3 | ~0.42 | ~30 |
| CAO-1 | 522.8 | ~7.2 | ~0.36 | ~20 |
| DCAO | 492.7 | ~1.3 | ~0.064 | ~70 |
| DCAO-2 | 506.8 | ~1.1 | ~0.056 | ~80 |
| LDAO | 229.4 | ~1.0 | ~0.023 | ~100 |
| DDM | 510.1 | ~0.17 | ~0.0087 | ~70 |

$^a$Molecular weight of detergents.
$^b$Solubilization yield of LHI-RC complex from the membrane.

The CMC values of the DPA set were found to have a large variation, depending on the hydrophobic groups. DPA-2 with two benzene rings was estimated to be highest (~77.5 mM; ~2.5 wt. %), while DPA-3 with two cyclohexyl rings to be lowest (~4.9 mM; ~0.17 wt. %). DPA-1 was estimated to have an intermediate CMC value (~13 mM; ~0.42 wt. %). The rather large CMC values of DPA-2 relative to that of DPA-3 may be due to the polar character of benzene ring relative to cyclohexyl rings, thereby having a lower propensity for self-association. On the other hand, DCAO and CAO, with two and three hydroxyl groups in the lipophilic region, respectively, showed ~8 times difference in their CMC values (~1.0 mM and ~8.3 mM, respectively). The CMC value of CAO was similar to that of CHAPS (~8.0 mM), consistent with a general notion that a hydrophobic group is a main factor in detergent self-assembly behaviors.

The photosynthetic superassembly of R. capsulatus was employed to evaluate the new N-oxide amphiphiles and conventional detergents (LDAO and DDM). The native form of the superassembly consists of three components: the labile light harvesting complex I (LHI), the resilient reaction center complex (RC) and the most robust light harvesting complex II (LHII) (Chae et al., ChemBioChem 2008, 9, 1706-1709). The superassembly used for the study did not contain the LHII portion, which was removed via a genetic engineering (Laible et al., Biochemistry 2003, 42, 1718-1730). The resulting LHI-RC complex contains dozens of protein subunits with five different components, making it challenging to preserve its native quaternary structures. Mild detergents (e.g., DDM) maintain the native conformation of the LHI-RC complex, while detergents with intermediate strength (e.g., LDAO) destroy most LHI complexes with intact RC complexes. The use of harsh detergents such as sodium dodecyl sulfate (SDS) will destruct both structures of LHI and RC complex. Thus, the LHI-RC complex is an excellent system to classify a wide range of detergents according to their detergent strength.

The presence of various types of cofactors such as bacteriochlorophyll and carotenoids embedded in the complexes, thereby providing a well-featured UV-Vis absorption spectrum, facilitates the assessment of the protein integrity for a set of detergents via optical spectrophotometry. The native conformation of the protein is represented by a very strong peak at 875 nm in its absorption spectrum, while the intact RC but denatured LHI, or denatured LHI and RC, produce rather intense peaks at ~800 nm and ~760 nm, respectively. A previous study showed that DDM was a highly promising conventional detergent for solubilization and stabilization of the superassembly (Chae et al., ChemBioChem 2008, 9, 1706-1709), which is in a good agreement with a wide use of the agent in membrane protein science. In contrast, LDAO was shown to destroy the structural integrity of LHI-RC complexes.

Figure 3:
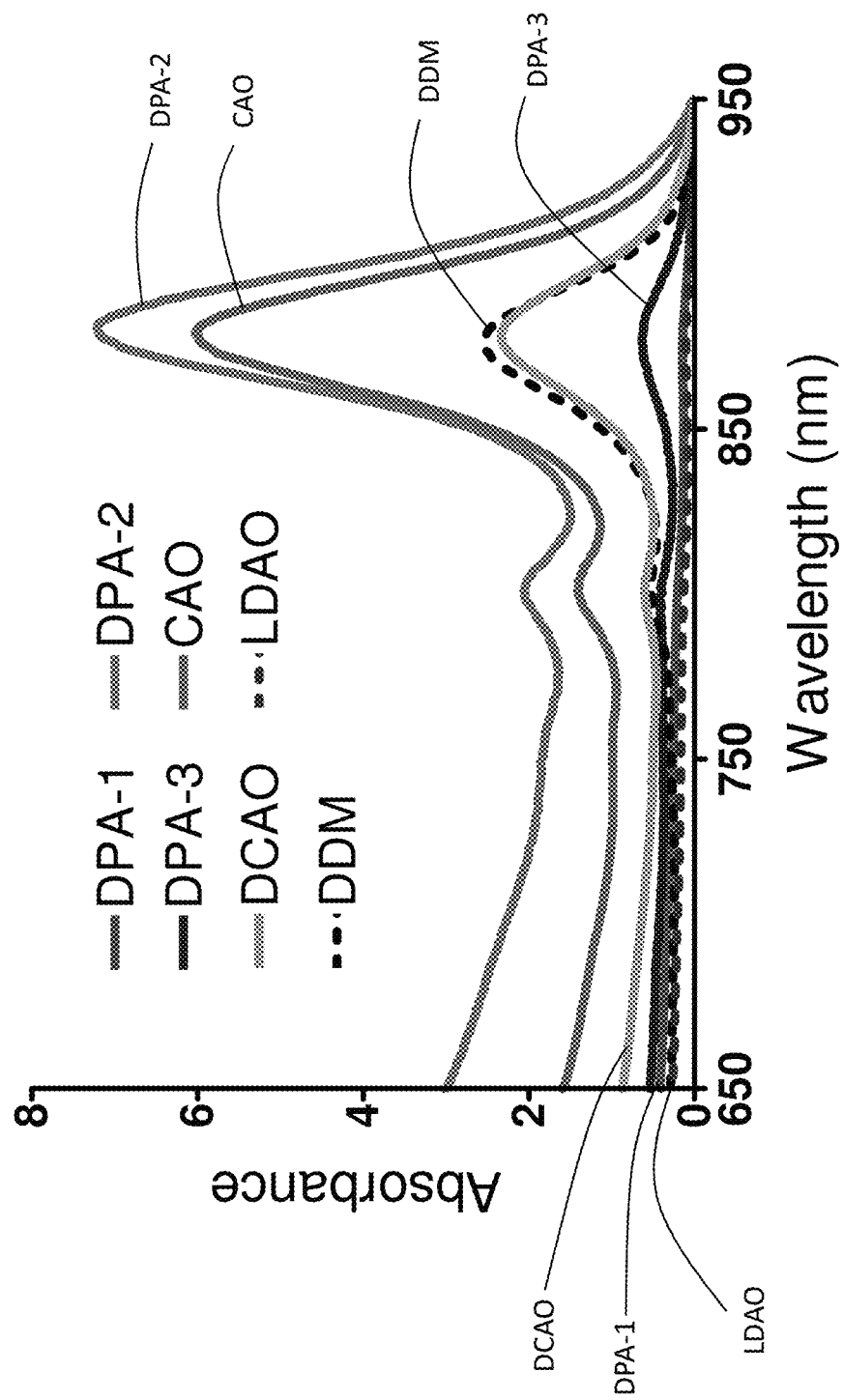
FIG. 3 is the spectra of homogenized membrane including LHI-RC complexes. This membrane part was not solubilized by detergent treatment during the solubilization process and was collected as a pellet after ultracentrifugation. Protein solubilization efficiencies in individual detergents were estimated by subtracting the amount still remaining in the homogenized pellets from the initial amount of photosynthetic superassembly. The pellets were homogenized prior to spectrum measurements.

These two reagents were chosen as control agents for the assay. For the superassembly solubilization, the intracytoplasmic R. capsulatus membranes enriched in LHI-RC complex were treated with 10×CMC individual new agents except DPA-2; DPA-2 was tested at 2×CMC based on its high CMC value. On the other hand, conventional detergents (LDAO and DDM) were used at 50×CMC due to the small CMC value in terms of wt. %. The solubilized protein portion and insolubilized part containing cellular debris and insolubilized membranes were separated via ultracentrifugation and isolated as the supernatant and pellet, respectively. The absorption spectra of these two portions were taken to assess detergents efficacy on the protein solubilization and stabilization. See FIG. 1A and FIG. 3.

For the purification, the detergent-solubilized protein samples were subjected to a metal affinity column chromatography and eluted with the elution buffer containing 1M imidazole and 1×CMC individual detergents. The UV-Visible spectra of the resulting protein samples were taken to investigate the integrity of detergent-purified LHI-RC complexes. See FIG. 1B and FIG. 4B. Consistent with previous results, LDAO extracted the complexes almost quantitatively (see FIG. 3 and Table 2.1), with the native protein conformation mostly destroyed during the solubilization and purification processes (see FIG. 1B). A similar trend was observed for DPA-1, while DPA-3 displayed somewhat different behavior.

Figures 4A, 4B:
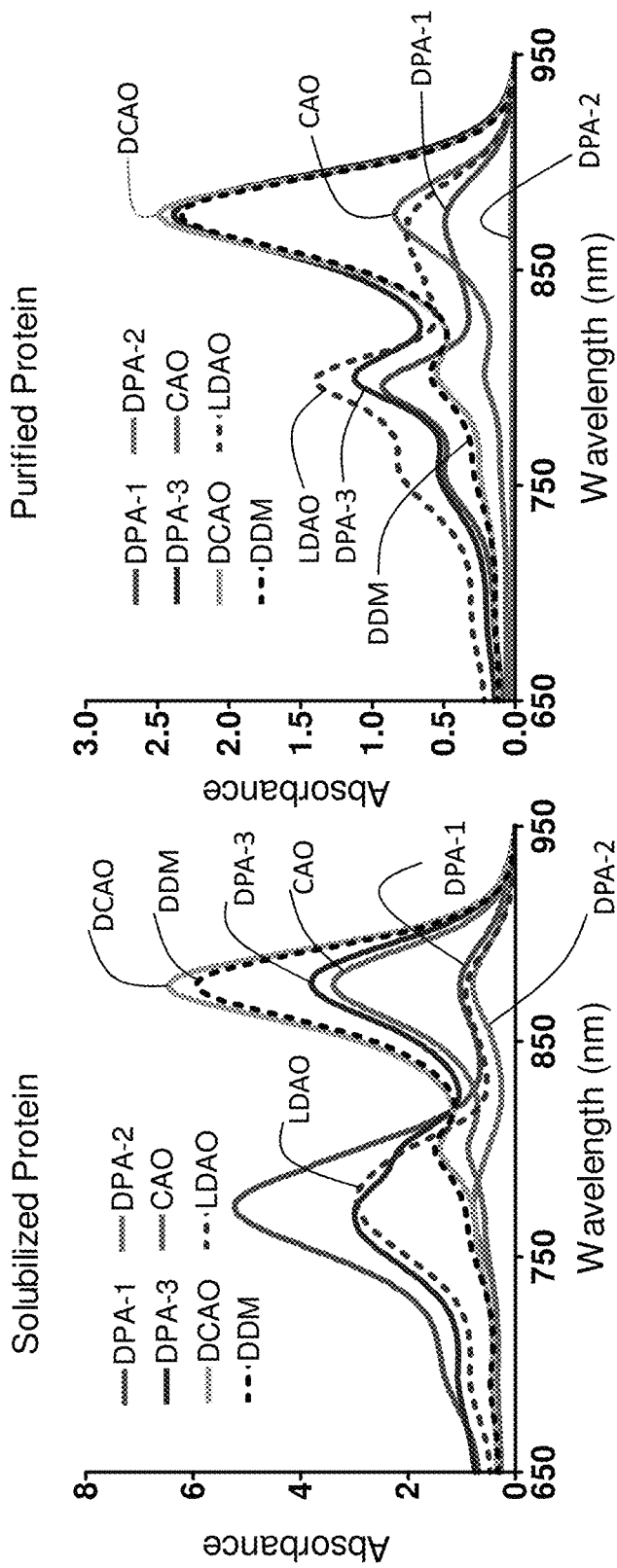
FIG. 4A is the spectra of solubilized supernatant for *R. capsulatus* superassembly in dipod amphiphiles (DPA-1, DPA-2 and DPA-3) and two of the novel N-oxide amphiphiles disclosed herein (CAO and DCAO) and two conventional detergents (DDM and LDAO).
FIG. 4B is the spectra of purified protein for *R. capsulatus* superassembly in dipod amphiphiles (DPA-1, DPA-2 and DPA-3) and two of the novel N-oxide amphiphiles disclosed herein (CAO and DCAO) and two conventional detergents (DDM and LDAO). For FIG. 4A, the solubilized supernatant was obtained by taking the soluble portion after ultracentrifugation of detergent-treated membrane samples. For FIG. 4B, the protein was purified via Ni-NTA affinity column and collected in the elution buffer containing 1M imidazole. UV-Vis spectra were taken in a range of 650 nm to 950 nm.

DPA-3 solubilized the LHI-RC complexes as efficiently as DPA-1 (FIG. 3; ~95-100%), but the protein degradation observed for DPA-3 was much less than that observed for DPA-1 latter and LDAO (FIG. 4A). Such enhanced stabilizing characteristic of DPA-3 relative to DPA-2 was also evident in the absorption spectra of the purified proteins. See FIG. 4B. DPA-2, with two phenyl group, failed to extract the complexes with any efficiently (~15%), and most of the extracted complexes underwent significant degradation.

The behavior of CAO and DCAO deviated significantly from that of the DPAs and LDAO, despite the shared N-oxide head group moiety. CAO and DCAO were somewhat less effective than DPAs and LDAO for the extraction of the LHI-RC complexes (~30% and ~70%, respectively), but the native structure of the complexes solubilized and purified by these reagents was fully retained as effectively as DDM. See FIGS. 1A and 1B. Furthermore, under the experimental conditions, DCAO did not form a hydrogel.

Figure 1C:
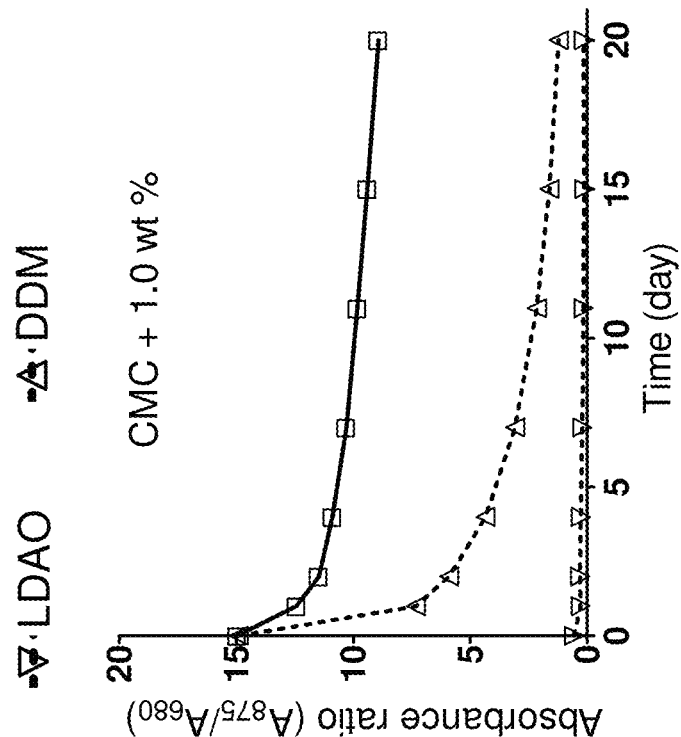
FIG. 1C is a graph depicting the long-term stability of the light harvesting complex I/resilient reaction center (LHI-RC) complexes in the four listed detergents at CMC+0.04 wt. %.
Figure 1D:
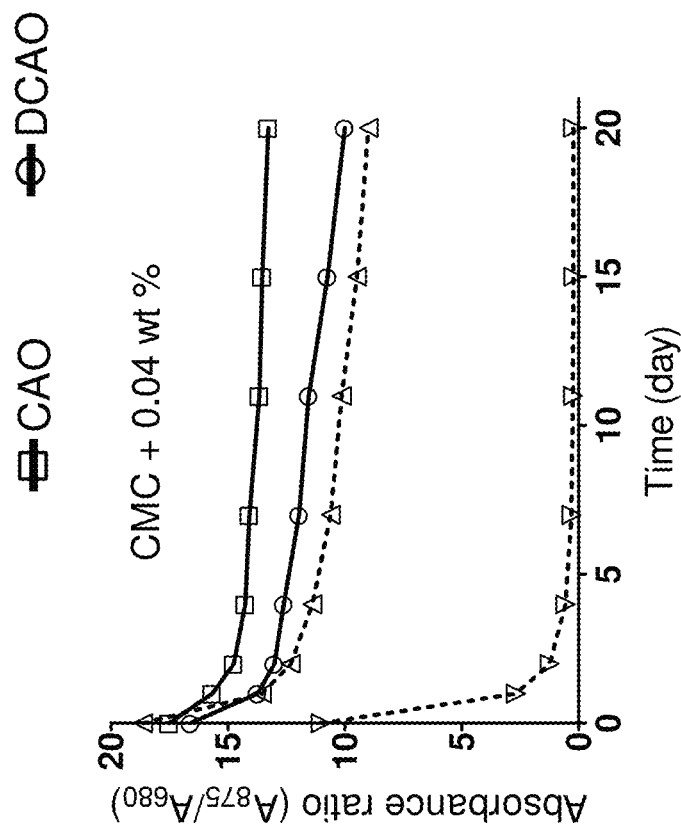
FIG. 1D is a graph depicting the long-term stability of Light Harvesting I-Reaction Center (LHI-RC) complexes in the four listed detergents at CMC+1.0 wt. %. In both figures, protein integrity in each agent was assessed by measuring absorbance ratio ($A_{875}/A_{680}$) over a 20-day incubation period at room temperature (~22° C.).

The favorable properties of CAO and DCAO in terms of membrane protein stabilization prompted further evaluation of these reagents' ability to stabilize protein superassemblies as a function of time. DDM-purified samples were diluted with solutions containing CAO or LDAO. The final detergent concentration in each sample was CMC+0.04 wt. % and the dilution resulted in residual DDM concentrations far below the DDM CMC (0.0004 wt. %). Protein stability was monitored over time at room temperature by measuring absorbance ratios (A875/A680) (absorption at 680 nm arises from the oxidation of bacteriochlorophyll dissociated from LHI upon denaturation). The CAO- and DCAO-solubilized superassemblies are more stable than DDM-solubilized protein with the best performance observed for CAO. See FIG. 1C. When the detergent concentration was increased to CMC+1.0 wt. %, the efficacy difference between CAO and DDM was more prominent. See FIG. 1D. Of note, DCAO was not evaluated in this long-term stability of the superassembly due to its high tendency to form a hydrogel at this high concentration.

Additional, data were obtained for the long-term stability of the superassembly using CHAPS and CHAPSO. After a 20 day-incubation at room temperature, CHAPSand CHAPSO-purified proteins retained ~65% of the native conformation. In constrast, CAOs-purified proteins preserved ~75% of their initial native structures. Thus, the CAOs are superior to CHAPS and CHAPSO in this regard. While the CAOs solubilized the complexes in ~30% yield (less than the ~50% solubilization efficiency for CHAPS and CHAPSO), membrane protein stabilization efficacy is considered to be more important than solubilization efficiency. That is, there is an overall performance trade-off: high solubilization efficiency matters little if the native conformation of the protein is lost in the solubilization process.

While not being bound to any specific molecular mechanism or phenomenon, it is believed that relatively small size of the N-oxide head groups of the compounds disclosed and claimed herein (as compared to that of a sulfobetaine) is the source of their functional advantage. The hydrophilic groups of a detergent interact with the hydrophilic domains of membrane proteins. However, in the case of membrane-bound proteins, the hydrophobic group of detergents will also be interacting with the hydrophobic surface of membrane proteins. These two interacting domains will be in close physical proximity. That is, it is thought that the hydrophilic domain of a membrane-bound protein interacts with the hydrophilic head group of a detergent at a point very near the hydrophilic-hydrophobic borderline in the membrane-bound protein. Thus, the N-oxide head group, having smaller relative size, covers a relatively smaller area of the protein's exposed and accessible hydrophilic domain. This leaves more of the protein's hydrophilic surface area exposed and available for protein-protein interaction (as contrasted to protein-detergent interaction). The hydrophilic-hydrophilic interactions between two or more membrane-bound proteins (which are in the process of being solubilized or are already solubilized by interaction with the detergent) are thought to induce an initial protein-protein interaction event that leads to nucleus formation and crystal lattice formation.

In an effort to enhance detergent properties and to exclude the water-solubility issues associated with DCAO, analogs of CAO and DCAO were prepared. These amphiphiles are designated as CAO-1, DCAO-1 and DCAO-2 (Scheme 2-3). These agents share the hydrophobic groups with their original compounds, CAO and DCAO, but vary in the hydrophilic group. CAO-1 and DCAO-1 have an additional methyl group on amide nitrogen, while DCAO-2, a constitutional isomer of DCAO-1, contains an ethyl group on amide nitrogen with the chain length between the amide and the head group shorter by one carbon than other CAO and DCAO derivatives.

Figures 2A, 2B:
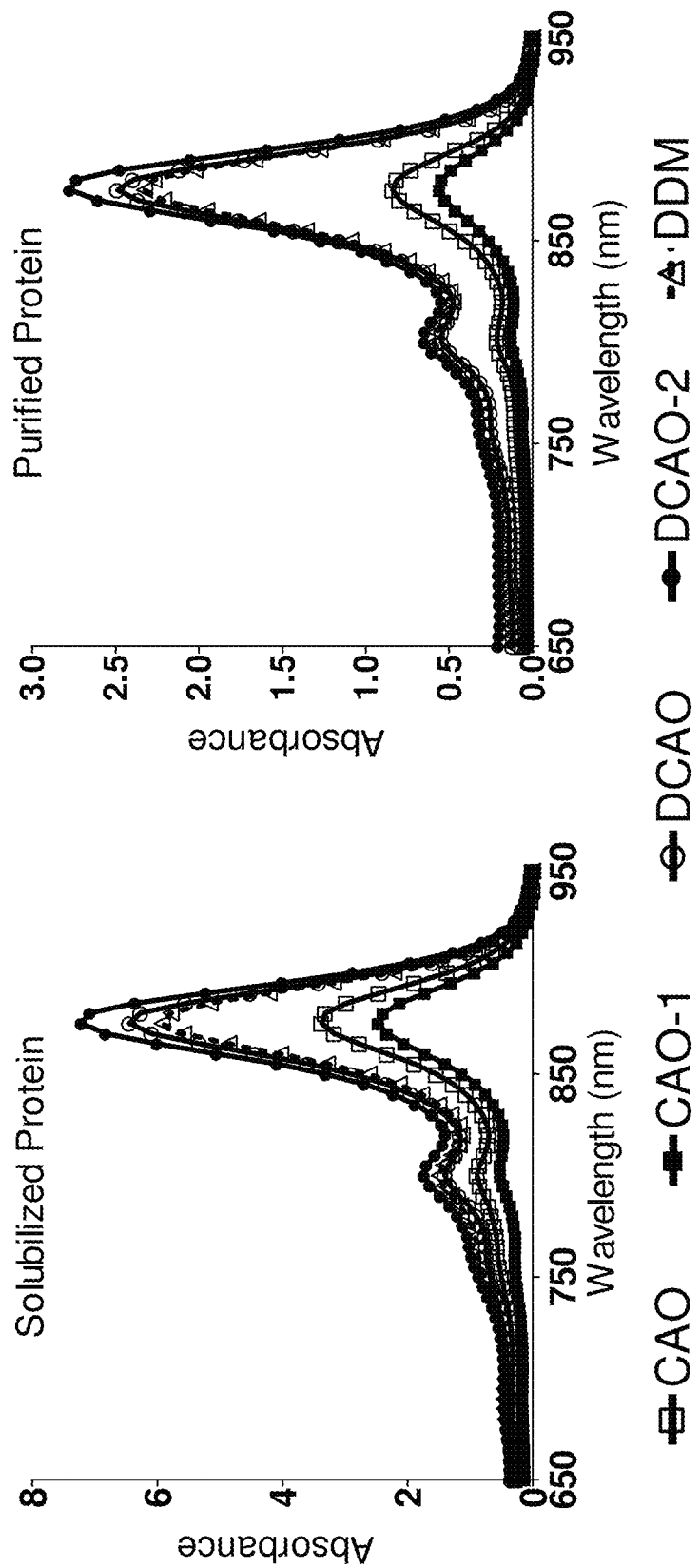
FIG. 2A is the absorbance spectra of *R. capsulatus* superassembly solubilized in four of the novel N-oxides (CAO, CAO-1, DCAO, and DCAO-2) and a conventional detergent (DDM).
FIG. 2B is the absorbance spectra of *R. capsulatus* superassembly purified in four of the novel N-oxides (CAO, CAO-1, DCAO, and DCAO-2) and a conventional detergent (DDM). In both figures, the detergents were used at 2×CMC for CAO and CAO-1, 10×CMC for DCAO and DCAO-2, and 50×CMC for DDM. The protein complexes were purified by using Ni-NTA affinity column and the protein complexes were eluted from the resin in the detergent concentration at 1×CMC.
Figure 5:
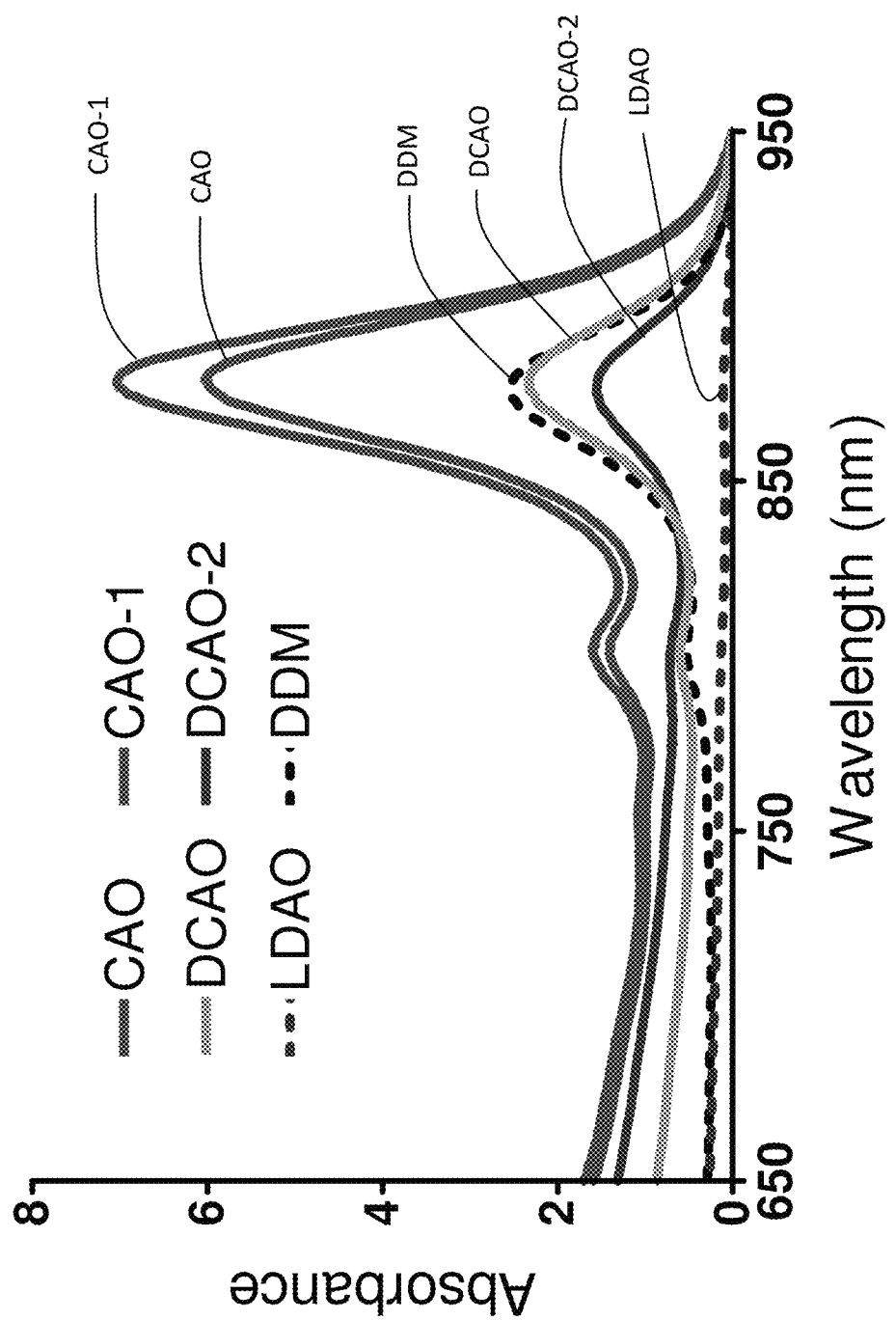
FIG. 5 is the spectra of homogenized membranes including LHI-RC complexes. This membrane part was not solubilized by detergent treatment during the solubilization process and was collected as a pellet after ultracentrifugation. For the complex solubilization, N-oxide amphiphiles (CAO, CAO-1, DCAO and DCAO-1) and two conventional detergents (DDM and LDAO) were used. Protein solubilization efficiencies in individual detergents were estimated by subtracting the amount still remaining in the homogenized pellets from the initial amount of photosynthetic superassembly. The pellets were homogenized prior to spectrum measurements.

DCAO-1 showed limited solubility in water while DCAO-2 was water-soluble well up to 5 wt. %. Both agents did not form a hydrogel at the same concentrations that DCAO does. The CMC values were determined for CAO-1 (~7.2 mM; ~0.38 wt. %) and DCAO-2 (~1.1 mM; ~0.056 wt. %), which are similar to those of their parent compounds, CAO and DCAO, respectively (see Table 2.1 above). When these new derivatives were evaluated for the LHI-RC complexes, the agents displayed somewhat different behaviors from their parent compounds in terms of protein solubilization efficiency. See FIG. 5. CAO-1 was rather inferior to CAO (20% vs. 30%), while DCAO-2 was superior to DCAO (80% vs. 70%). However, no appreciable differences were observed in the protein stabilization efficacy between the derivatives and the respective originals. All of these cholate and deoxycholate-based agents preserved the native conformation of the superassembly during protein solubilization and purification processes. See FIGS. 2A and 2B.

Figures 2C, 2D:
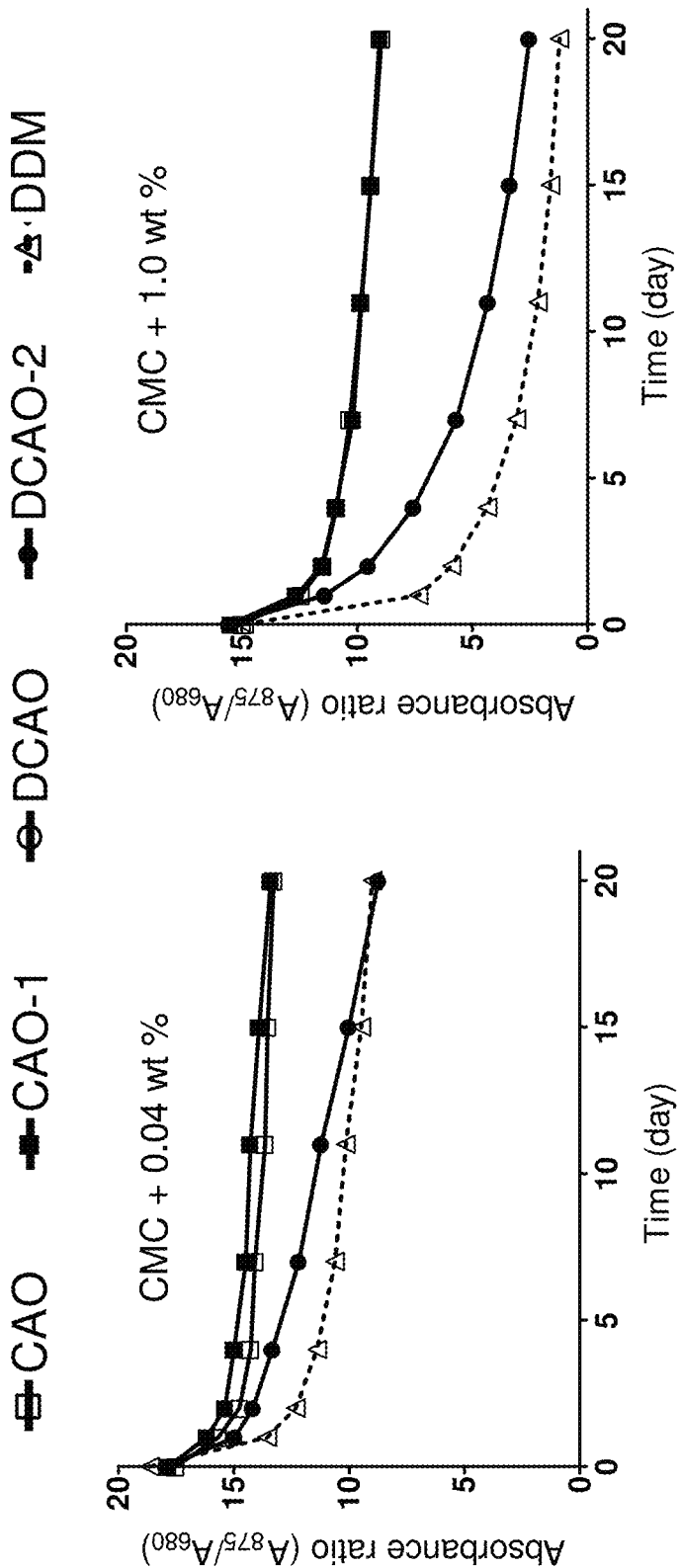
FIG. 2C is a graph depicting the long-term stability of light harvesting complex I/resilient reaction center (LHI-RC) complexes in a detergent concentration of CMC+0.04 wt %.
FIG. 2D is a graph depicting the long-term stability of light harvesting complex I/resilient reaction center (LHI-RC) complexes in a detergent concentration of CMC+1.0 wt %. In both figures, protein integrity in each agent was assessed by measuring absorbance ratio ($A_{875}/A_{680}$) over a 20-day incubation period at room temperature.

When these agents were evaluated for the long-term stability of the superassembly, only minimal difference were observed between the new derivatives (CAO-1 and DCAO-2) and the respective originals (CAO and DCAO), but detergent efficacy could be differentiated between the cholate- and deoxycholate-based amphiphiles. Cholate-based agents appeared to be superior to deoxycholate-based compounds in this respect. With regard to a comparison with DDM, it is notable that DCAO-2 slightly outperformed this conventional detergent at CMC+0.04 wt. % and CMC+1.0 wt. %. CAO and CAO-1 were clearly superior to DDM at both concentrations. See FIGS. 2C and 2D. DCAO was not included in this long-term stability evaluation because this agent tends to form a hydrogel during long-term storage.

In spite of the usefulness of CHAPS, structural analogues of CHAPS have rarely been explored for their potential as membrane protein extraction and stabilization reagents. Systematic investigation and thorough data analysis have not been conducted to pinpoint structural traits that are responsible for the favorable behavior of this general class of amphiphiles. Described herein are variations of hydrophobic moieties of N-oxide amphiphiles and their resulting properties, as evaluated by several methods. Cholate-based agents are highly effective in the stabilization of membrane proteins, whereas deoxycholate-based amphiphiles are highly effective for both the solubilization and stabilization of membrane proteins. Accordingly, these amphiphiles can serve as research tools and as alternatives to conventional detergents in a variety of membrane protein manipulation techniques.

With the exception of DDM, all amphiphiles investigated in this current study share N-oxide as the hydrophilic group, but the amphiphiles vary in their hydrophobic portions. The variations range from a C12 alkyl chain (LDAO) to two-ring systems (DPA-1, DPA-2 and DPA-3) to multiple-fused ring systems with a various number of hydroxyl group(s) (CAO, CAO-1, DCAO and DCAO-2). When these N-oxide amphiphiles were evaluated for the solubilization and stabilization of LHI-RC complexes, the amphiphiles displayed a large variation of behaviors depending on the hydrophobic group architecture. This result indicates the prominent roles of the hydrophobic groups in membrane protein manipulation. LDAO and DPAs, with the exception of DPA-2, appeared to almost quantitatively solubilize LHI-RC complexes from the membrane, although most of LHI-RC complexes lost their native structures after this process.

Among the three DPAs, DPA-2-solubilized complexes were the least destabilized, indicating that this agent may find its utility in other studies with rather stable membrane proteins. In contrast, the cholate- and deoxycholate-based amphiphiles were less efficient than DPAs and LDAO in solubilizing the LHI-RC complexes but the native conformation of the solubilized superassembly was well maintained.

A substantial difference between cholate- and deoxycholate-based amphiphiles was also found in the superassembly solubilization and long-term stability experiments. The deoxycholate-based amphiphiles (DCAO and DCAO-2) were superior to the cholate-based amphiphiles (CAO and CAO-1) in the protein solubilization efficiency but inferior to the latter in the long-term protein stabilization efficacy. It is notable that DCAO-2 displayed favorable behaviors in the superassembly for both solubilization and stabilization. The cholate-based amphiphiles CAO and CAO-1 are especially promising in stabilizing the complexes, although their solubilization efficiencies were similar or less effective than DDM.

The favorable behaviors of cholate- and deoxycholate-based N-oxide amphiphiles for the superassembly can be traced to the interplay of their structural characteristics. These structural characteristics include the presence of one or more hydroxyl groups in the lipophilic region, the facial orientation of the polar hydroxyl groups, and/or the presence of a multi-fused ring system. Among these features, the first one is particularly interesting because some recently developed agents contain similar structure motifs. For instance, short peptide designers (e.g., V6D) have multiple amide groups over the lipophilic backbone while GLCs/GDN contains an ether type of groups at the end of the hydrophobic groups; see FIG. 6 (Zhao et al., *Proc. Natl. Acad. Sci. U.S.A.* 2006, 103, 17707; Chae et al., *Chem.-Eur. J.* 2012, 18, 9485-9490, respectively). Tandem facial amphiphiles (TFAs) bear two amide linkages at the center region of the hydrophobic moiety (Chae et al., *J. Am. Chem. Soc.* 2010, 132, 16750).

Figure 6:
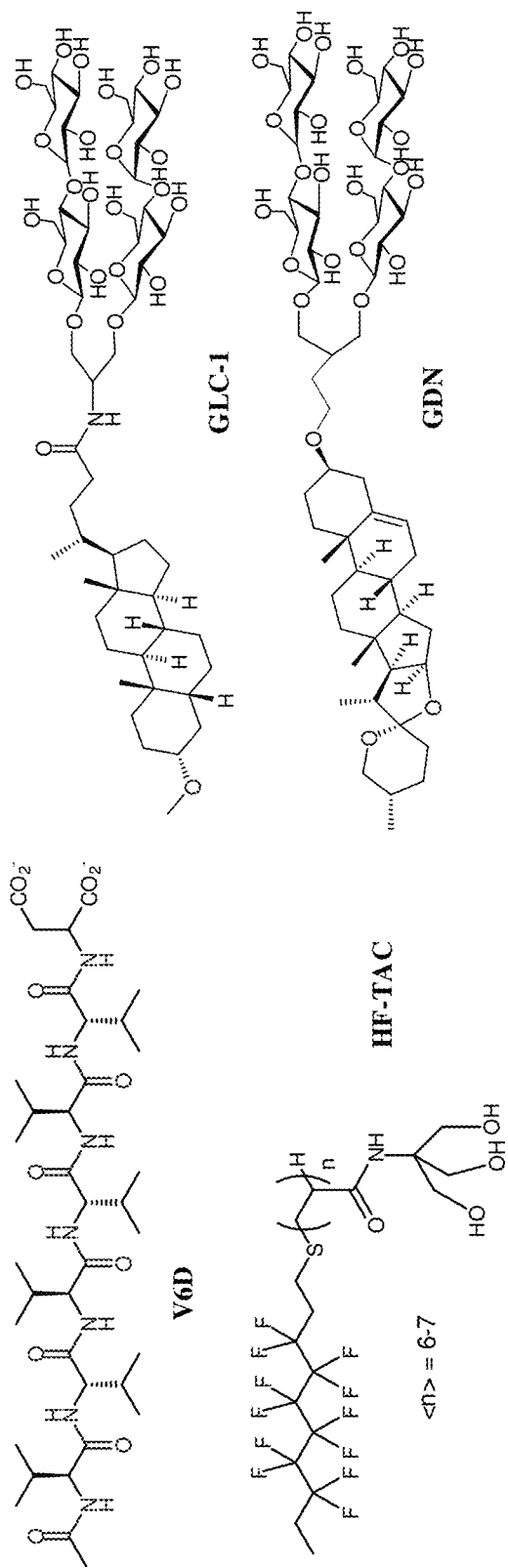
FIG. 6 depicts chemical structures of recently-developed novel classes of amphiphiles containing relative lipophobic groups (e.g., ether, amide, fluorinated alkyl chain). These amphiphiles were shown to have mild properties in terms of membrane protein stabilization.
Figure 6:
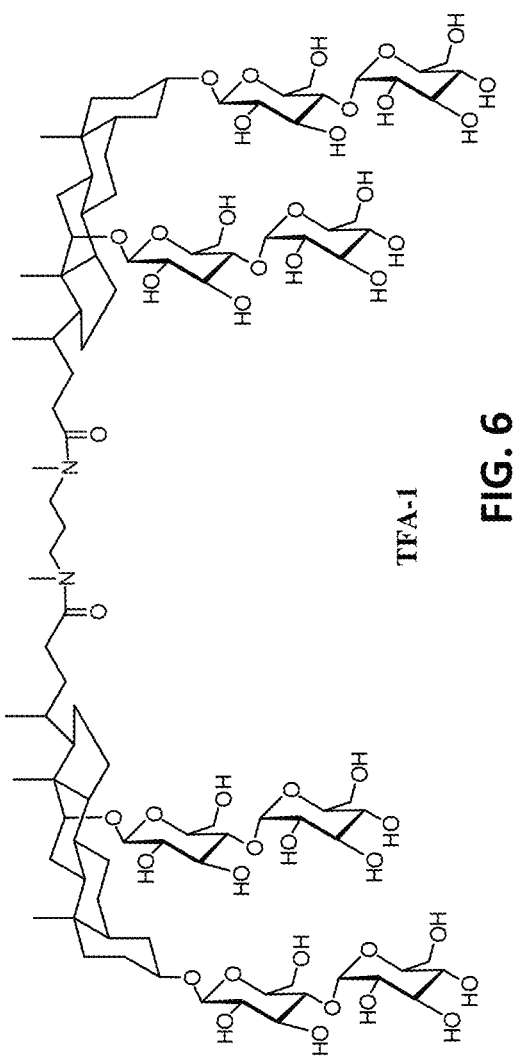

These functional groups (i.e., amide and ether groups) are polar relative to hydrocarbons. Accordingly, these non-hydrocarbon groups-containing hydrophobic parts are less hydrophobic than the counterparts with no such groups, thus being relatively lipophobic. A similar characteristic can be also found in a hemifluorinated alkyl chain that is lipophobic but hydrophobic (Breyton et al., *FEBS Lett.* 2004, 564, 312; Popot et al., *Annu. Rev. Biophys.* 2011, 40, 379). Hemifluorinated alkyl chains were successfully used for the development of HFSs with mild properties; FIG. 6. Of note, the agents mentioned above share the presence of lipophobic moieties (e.g., alcohol, ether, amide, or fluorine atoms) in their hydrophobic regions, although their lipophobicities are different, and were shown to be mild enough to retain the native structures of various membrane proteins.

The experiments described herein show that the presence of such lipophobic groups in the hydrophobic region can modulate the interaction of these amphiphiles with the hydrophobic surface of membrane proteins. Because detergent-protein interaction strength should be modulated for the best performance, it is likely that there is an optimum range for the number of those lipophobic groups. This optimal number would be dependent on various factors including a) which lipophobic group are present, b) where the group is located in the hydrophobic region, c) which target protein are being dealt with, and d) what kind of protein manipulation are being conducting.

Dependence on these variables was illustrated by the results of several studies described herein. For example, the cholate-based amphiphiles with three hydroxyl groups were most favorably behaved for protein stabilization, while the deoxycholate-based amphiphiles with two hydroxyl groups were more effective than the former in the superassembly solubilization. Similarly, the amphiphile F4-HF-MNG with 4 fluorine atoms on benzene ring was superior to F12-HF-MNG with 12 fluorine atoms for the stabilization of the same complexes (Cho, Byrne, and Chae, *ChemBioChem* 2013, 14, 452). A similar phenomenon was observed in the comparative study of HFSs to FSs; HFSs with an alkyl tips, thus containing fewer fluorine atoms, were superior to fully-fluorinated HFs with regard to membrane protein stabilization (Popot et al., *Annu. Rev. Biophys.* 2011, 40, 379).

The zwitterionic detergent LDAO is known to be rather harsh in membrane protein manipulation (McGregor et al., *Nat. Biotechnol.* 2003, 21, 171)., therefore nonionic detergents such as OG and DDM have been preferred for membrane protein research. Interestingly, CHAPS with a zwitterionic sulfobetaine head group often displayed favorable behaviors similar to non-ionic detergents in membrane protein stabilization, resulting in its wide-ranging use as an additive in membrane protein manipulation. A similar result was observed in the laboratories of the inventors. CHAPS could extract LHI-RC complexes without structural degradation, although the solubilization yield was rather low (~50%). This low solubilization yield prompted the inventors to direct their attention to evaluating a structural origin for this favorable behavior.

Protein Solubilization and Stabilization Protocols.

The solubilization and purification of the *R. capsulatus* superassembly were conducted according to the published protocol (Chae et al., *ChemBioChem* 2008, 9, 1706-1709). First, specialized photosynthetic membranes called intracytoplasmic membranes were obtained from an engineered strain of *Rhodobacter* (R.) *capsulatus*, U43[pUHTM86Bgl], lacking the light-harvesting complex II (LHII). The solubilization experiment began by thawing and homogenizing frozen aliquots of *R. capsulatus* membranes at room temperature. The solution was then incubated with mild agitation at 32° C. for 30 min. Subsequently, the solution was further incubated for 30 min after adding individual detergents (2×CMC for DPA-2, CAO and CAO-1, 10×CMC for DPA-1, DPA-2, DCAO and DCAO-2, 50×CMC for DDM and LDAO) into 1.0 mL solutions of *R. capsulatus* superassembly. The solution was then subjected to ultracentrifugation at 310,000 g at 4° C. for 30 min to remove membrane debris.

The spectra of solubilized supernatant and solubilized pellet were taken in a range from 650 nm to 950 nm after being homogenized. For the purification of the protein, detergent-solubilized samples were transferred into a new 1.7 mL microcentrifuge tube containing Ni-NTA resin (Qiagen, Inc.; Valencia, Calif.; pre-equilibriated and stored in an equal volume of buffer containing 10 mM Tris, pH 7.8, and 100 mM NaCl). Following one-hour incubation at 4° C. for protein binding, the resins were collected and washed twice with 0.5 mL of binding buffer (a pH 7.8 Tris solution containing DDM at 1×CMC). Purified protein solution were collected by eluting three times with 0.20 mL elution buffer solutions containing 1 M imidazole (otherwise, this buffer was identical to binding buffer; the pH of each solution was readjusted to pH=7.8) and diluted with 0.4 mL of the binding buffer to reach 1.0 mL solution. UV-Vis spectra of the superassembly purified in individual detergents were then taken to assess the stability of the protein.

Long-Term Stability Evaluation.

R. capsulatus superassembly was purified in DDM according to the protocol described above. The DDM-purified sample was then diluted to the solutions containing individual detergents (CAO, CAO-1, DCAO, DCAO-2, DDM and LDAO). The dilution makes DDM concentration reached far below its CMC and the final individual detergent concentration at CMC+0.04 wt % or CMC+1.0 wt %. The spectra of individual detergents-solubilized LHI-RC complexes were taken in a range of 650 nm to 950 nm at regular intervals over 20 days during the incubation at room temperature. Protein integrity in each sample was assessed via changes in absorbance ratio ($A_{875}/A_{680}$) with time.

The studies described herein show that the presence and number of relatively lipophobic non-hydrocarbon groups (e.g., alcohols, ethers, or amides) in the lipophilic region play an important role in determining detergent properties. This structure-property relationship can be used to guide the modification of cholate amphiphiles to achieve certain desired membrane protein manipulation properties. In addition, CAOs and DCAOs can be used other arenas such as cell-free translation and micelle preparation, analogous to how the use of HFSs has been extended to producing membrane proteins in cell-free system, and to how CHPAS and CHAPSO have been used in capping the a patch of a lipid bilayer in micelle preparations.

In summary, hydrophobic variations of N-oxide amphiphiles have been prepared and their properties have been evaluated by several methods including their activity with a fragile superassembly, LHI-RC complexes. These results are informative for detergent structure-property relationships with respect to the effects of non-hydrocarbon group present in the lipophilic regions on membrane protein solubilization and stabilization.

Example 3

Solubilization and Purification of *Rhodobacter capsulatus* Membrane Proteins

A protocol has been developed to enable researchers to evaluate and determine the efficacy of detergents for use in solubilizing membrane proteins. The resulting classification is generally applicable to a wide range of detergents, including the amphiphiles of the invention. Detergents were tested with homogenized *Rhodobacter capsulatus* membranes containing photosynthetic protein superassemblies. The homogenate used (*Rhodobacter capsulatus* RC) is light sensitive therefore work should be carried out under low intensity light. Starting with protein complexes in their native lipid bilayer, two important detergent properties were tracked, allowing for a strength ranking to be assigned to any given detergent.

Amphiphile Screening and Stabilization:

Measurements. The starting material for the screening protocols and stability measurements included specialized photosynthetic membranes from an engineered strain of *Rhodobacter* (R.) *capsulatus*, U43[pUHTM86Bgl] (Kirmaier et. al. 2003. *Journal of Physical Chemistry B*. 106: 1799-1808), lacking the LHII light-harvesting complex. Membranes from this strain containing large quantities of the LHI-RC superassembly were isolated in advance, according to methods outlined by Laible and coworkers, and were flash frozen (Laible et al. 1998. *Biophysical Journal*. 74: 2623-2637).

To begin the solubilization and purification process, frozen aliquots of *R. capsulatus* membranes were thawed, homogenized, and equilibrated to 32° C. for 30 minutes. Disruption of the lipid bilayer and solubilization of the membrane protein complexes commenced with the addition of the desired amphiphile (compound of the invention) at a concentration of up to 100-fold higher than its CMC to 1 mL aliquots of the membranes. The efficacies of the amphiphiles saturated at relatively low concentrations, thus the quality and quantity of protein extracted did not change significantly at higher concentrations of amphiphile. For subsequent experiments, the amphiphiles were evaluated at 10-fold CMC during the solubilization step. The conventional detergent, DDM, was used at 100-fold CMC, which is the concentration typically used for membrane protein extraction (e.g., Chang et al., 1998 *Science*. 282: 2220-2226).

The membrane samples were allowed to incubate with the amphiphile for 30 minutes at 32° C. The solubilized material was then separated from the membrane debris in an ultracentrifuge at 315,000×g at 4° C. for 30 minutes. The pellet, containing membrane protein complexes not removed from the lipid bilayer, was resuspended and homogenized with 1 mL of 10 mM Tris buffer (pH 7.8) and 100 mM NaCl. After a UV-Vis-nearIR absorption spectrum was recorded, the resuspended pellet was discarded. The supernatant from the spin was pipetted into a new microcentrifuge tube containing Ni-NTA resin (Qiagen, Inc.; Valencia, Calif.; pre-equilibrated and stored in an equal volume of buffer containing 10 mM Tris, pH 7.8 and 100 mM NaCl). The tubes were then incubated and inverted for 1 hour at 4° C. During this period, only the reaction center bound to the Ni-NTA resin because of the engineered hepta-histidine tag on the C-terminus of the M subunit (Goldsmith et al. 1996. *Biochimica et Biophysica Acta*. 1276: 171-175; Pokkuluri et al. 2002. *Biochemistry*. 41: 5998-6007; Kirmaier et al., 2003 *Chemical Physics*. 294: 305-318).

Once binding was complete, samples were loaded onto resin-retaining spin columns (e.g., emptied His Spin Trap™ columns; GE Healthcare). The columns were then inserted into a 2 mL microcentrifuge tube to retain the filtered solution during centrifugation. Samples were rinsed twice with 0.5 mL of amphiphile-containing binding 15 buffer (a 7.8 pH Tris solution containing the amphiphile used for solubilization at its CMC). Finally, protein was eluted into a fresh microcentrifuge tube with three 0.2 mL elution buffer aliquots (this buffer was identical to binding buffer with the addition of 1 M imidazole).

The *R. capsulatus* LHI-RC complexes extracted and purified by this procedure contain large numbers of cofactors that have absorptions at distinct wavelengths, and each component of the LHI-RC superassembly has a different inherent stability outside the lipid bilayer. The solubilization protocol outlined above therefore provides a multifaceted assessment of the efficacy of conventional detergents and novel amphiphiles. UV-Vis absorption spectroscopy data obtained at various stages of the protocol allow one to determine which protein components have degraded at these stages. The results reveal the relative potency of amphiphiles in disrupting a lipid bilayer and subsequently stabilizing the photosynthetic superassembly or subunits thereof. The disruption potential was measured as the yield of superassembly extracted during solubilization (or, alternatively and more precisely, as the absence of superassembly in the pellet from the spin following solubilization).

The stabilizing propensity was determined from the spectra of the purified protein. An amphiphile was judged to be mild and stabilizing if it allowed the purification of fully intact LHI-RC superassembly (dominant absorption band at 875 nm). An amphiphile was judged to be strong and destabilizing if it resulted in little or no purified protein with absorption in the near IR, or led to isolation of the intact RC (which is relatively robust) in the absence of LHI. In this latter case, the RC was often damaged, as indicated by a large absorption at 760 nm (released co-factors) or dominant absorption at 800 nm with a shoulder at 850 nm, which indicates that the functional RC remains but it has lost a lipid that is normally bound tightly when the RC resides in its native lipid bilayer (Wang et al., 1994. *Photosynthesis Research*. 42: 203-215). An amphiphile was judged to be of intermediate strength if it allowed for the purification of fully intact RC with damaged or missing LHI (dominant absorption at 800 nm with a shoulder at 875 nm; damaged LHI still bound to RC absorbs 20 at 760 nm).

Similar criteria and protocols were used to judge the ability of amphiphiles to maintain solubilized and purified superassembly for extended periods. In this case, UV Vis-nearIR spectra were recorded at regular intervals. The degradation of the material could be monitored with the $A_{875}/A_{680}$ absorbance ratio, which decreased with time and sample integrity as the dominant 875 nm absorption of intact LHI disappeared and a 680 nm band appeared, indicating the presence of unbound, oxidized cofactors.

Figure 7:
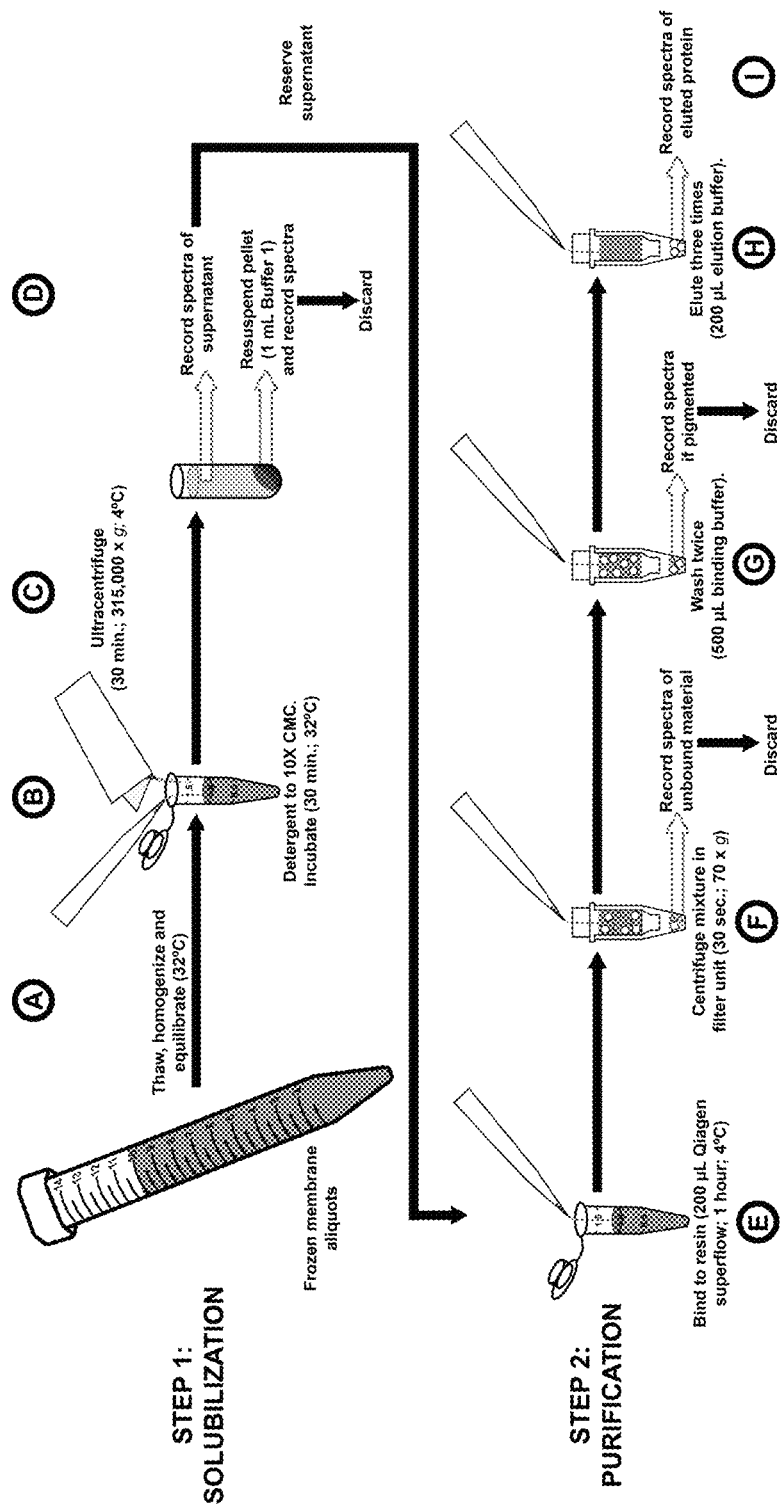
FIG. 7 is a schematic diagram illustrating the solubilization and purification steps employed in the assay described in Example 2.
Figure 8:
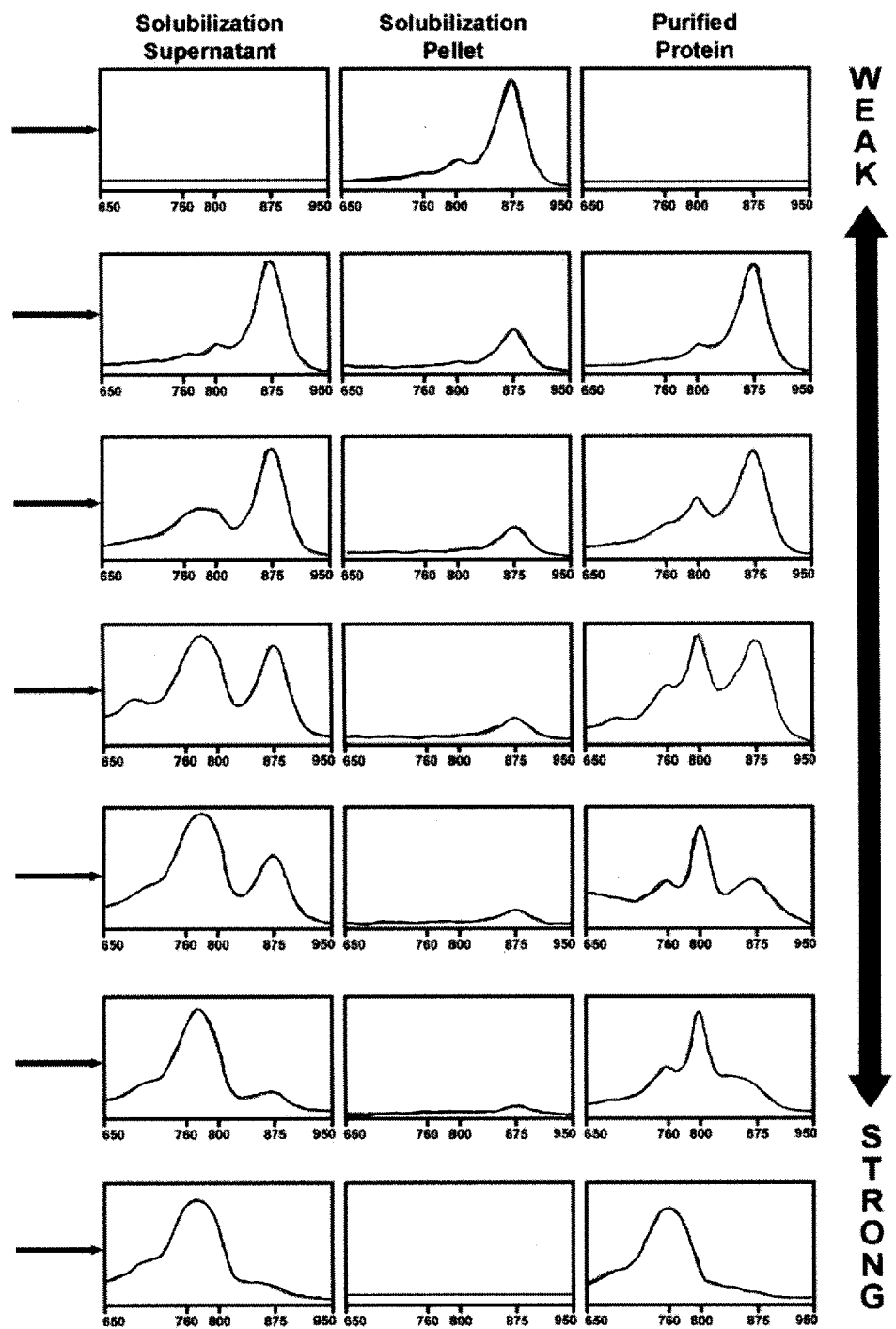
FIG. 8 is a flow chart for classification of amphiphilic compounds in the assay described in Example 2. Class determinations were based quantitatively on a specific absorbance ratio ($A_{875}/A_{760}$). The ratio of a sample of completely folded and functional superassembly can be >14.5; this ratio declines dramatically as the multi-subunit complex disassembles and denatures.

Protein Solubilization and Purification Using Amphiphiles Disclosed Herein:

First, solubilization (illustrated in "STEP 1" of FIG. 7) denotes the ability of a surfactant to penetrate, integrate and disrupt a lipid bilayer. This ability is demonstrated by the intensity of the spectral absorption bands of the Solubilization Supernatant (SS) and the Solubilization Pellet (SP). Secondly, the ability of micelles of the test surfactant to stabilize a membrane protein outside of a lipid bilayer can be assayed. For the second type of rating (illustrated in "STEP 2" of FIG. 7), spectra of the Purified Protein (PP) are used. Thus, FIG. 7 provides a graphical depiction of the following detailed steps for protein solubilization and purification, and the procedure for assigning a level to a particular detergent is illustrated in the flowchart of FIG. 8.

Step 1: Solubilization.

The following procedure can be used to evaluate solubilization properties of a detergent. The specific amounts of reagents, times, temperatures, and pH can be varied depending on various experimental factors such as the amount of homogenate available, the amount of detergent available, and the like, as would be readily understood by one skilled in the art. Solubilization Evaluation Procedure:

A) Thaw a 10 mL aliquot of *Rhodobacter capsulatus* RC homogenate ($OD_{875}$ 7.5). Although the membranes may be homogenized once prior to freezing, use a small volume glass tissue homogenizer to uniformly distribute the membrane suspension a second time after it has completely thawed. Equilibrate the homogenate to an appropriate temperature (32° C.) by inverting the entire sample in an Enviro-Genie® refrigerated incubator (or similar machine that allows inversions at a controlled temperature) for at least 30 minutes.

B) Divide the homogenate into 1 mL aliquots (to allow for ten possible screens for one tube of membrane stock) in microcentrifuge tubes. Add the detergent of interest at 10×CMC. Invert in the Enviro-Genie® refrigerated incubator for 30 minutes at 32° C. Use at least two controls (for example, LDAO and n-dodecyl-β-D-maltopyranoside) and one blank (no detergent) to ensure that data can be reliably evaluated.

C) Place the solubilized membrane suspension in a polycarbonate ultracentrifuge tube. Pellet the membrane debris in a tabletop ultracentrifuge at 315,000×g (for example, an Optima™ TLX tabletop ultracentrifuge; TLA 120.2 rotor; 85K rpm) for 30 minutes at 4° C.

D) Record a spectrum (from 650 nm to 950 nm) of the solubilized supernatant (SS), then reserve the supernatant for purification (STEP 2 below). Using a small glass homogenizer, resuspend the remaining pellet with 1 mL of buffer containing 10 mM Tris, pH 7.8 and 100 mM NaCl. Record a spectrum of the resuspended pellet (SP). Dilute to appropriately remain within the dynamic range of the spectrophotometer employed. The resuspended pellet can be disposed of after the spectrum has been recorded.

The 875 nm peak from the spectrum of the Solubilization Pellet of the blank (no detergent) is used to determine the percentage of complexes that were extracted from samples incubated with detergent. If the 875 nm peak of an experimental sample is at or above 50% of the blank peak, the detergent obtains an "S" rank to indicate the majority of the complexes were extracted after solubilization and reside in the supernatant. Conversely, a detergent obtains the rank of a "P" if peaks are below 50% of the blank peak, indicating the detergent is too weak to effectively penetrate, integrate and disrupt the lipid bilayer, leaving the majority of the complexes within the pellet.

Step 2: Purification.

E) Transfer each SS from step "D" into fresh and separate microfuge tubes. Invert a stock of Ni-NTA resin (Qiagen, Inc.; Valencia, Calif.; prequilibriated and stored in an equal volume of buffer containing 10 mM Tris, pH 7.8 and 100 mM NaCl) until the beads are completely mixed throughout the storage solution. Then add 200 µL of the Ni-NTA resin to each tube containing SS (so that one obtains 100 µL of resin in the tube). Invert the microfuge tubes containing the SS+resin in an Enviro-Genie® refrigerated incubator (or equivalent) for 1 hour at 4° C. to allow ample time for the histidine-tagged complex to bind to the resin.

F) His-Spin Trap™ columns (GE Healthcare, Pittsburgh, Pa.) can be used to purify the protein. These columns are pre-packaged with resin in place. Previous experiments indicated that the resin supplied with the His-Spin Trap™ columns does not bind proteins as well as the Ni-NTA Qiagen resin (necessitating the addition of the Qiagen resin in step "E"). These columns are used for the ease of washing and eluting the Ni-NTA resin, however the resin originally received with these columns is not used in this procedure. If a new His-Spin Trap™ column is being used, remove and discard the top cap and break off the bottom closure. Clean and rinse the column using water so that no resin remains.

Place the column in a 2 mL microcentrifuge tube to collect the liquid during centrifugation. Add 500-600 µL (when maximum column volume is 600 µL) of the SS to the column and centrifuge for 30 seconds at 70×g. Remove the flow-through and reserve it in a separate tube. Add any remaining SS and centrifuge again. Two spin cycles are typically required to centrifuge an entire sample. Combine all of unbound material. Although the flow-through from these spins is not used to determine detergent strength, spectra can be recorded to observe elements that did not bind to the column during purification. These spectrum profiles can also help determine if a particular detergent is interfering with affinity chromatography and is not allowing the histidine-tagged reaction center to properly bind to the nickel-charged resin. Once a spectrum of the unbound material has been recorded, it can be discarded.

G) Wash the column resin by adding 500 μL binding buffer (a 7.8 pH, 10 mM Tris solution containing 1×CMC of the detergent used for solubilization) to the column. Centrifuge for 30 seconds at 70×g. Repeat this step to wash the column a second time. If significant pigmentation is noticed in the column washes, record its spectrum. Otherwise, the eluent may be discarded.

H) Use a new 2 mL microcentrifuge tube for this step. Use of new tubes avoids contamination of the purified protein with any residual material that was rinsed off during the column wash. After the column is placed in a new 2 mL microcentrifuge tube, elute the target protein by subjecting the bound protein and resin to three separate aliquots of 200 μL of elution buffer (the binding buffer with the addition of 1 M imidazole). Centrifuge the column for 30 seconds at 70×g between each addition of elution buffer. If a stock Tris solution already at a pH of 7.8 is being used for the buffers, ensure that the pH of this solution is adjusted again to 7.8 after the addition of imidazole.

I) To facilitate spectroscopy, add 400 μL of binding buffer to the purified protein to adjust the volume of 1 mL. Record a spectrum of the purified protein. The reference is a solution containing 10 mM Tris, pH 7.8. From the spectrum of the purified protein, each detergent can be classified into one of six categories (weak to strong detergent) according to the flowchart in FIG. 8.

TABLE 3-2

CMC values and class evaluation for *R. capsulatus* superassembly.

| Detergent | M.W. | CMC (mM) | CMC (%) | Class |
|---|---|---|---|---|
| CAO | 508.7 | 7.1 | 0.36 | P1 |
| DCAO | 492.7 | 1.0 | 0.049 | S1 |
| CHAPS | 614.9 | 8 | 0.49 | S1 |
| CHAPSO | 630.9 | 8 | 0.5 | S1 |

Table 3-2 shows the CMC values and class evaluation for the *R. capsulatus* superassembly for CAO and DCAO in comparison to the commercial detergents CHAPS and CHAPSO. CAO and DCAO both have lower CMC values than CHAPS and CHAPSO. Additionally, DCAO is assigned to the same detergent class as CHAPS and CHAPSO, while providing a significantly lower CMC than CHAPS and CHAPSO. The lower CMC values indicate that less detergent is required for manipulating membrane proteins. Lower amounts of detergent can simplify characterization and analysis of the membrane proteins, indicating the value of the new detergents disclosed herein.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the following claims.

What is claimed is:

1. A compound of Formula I:

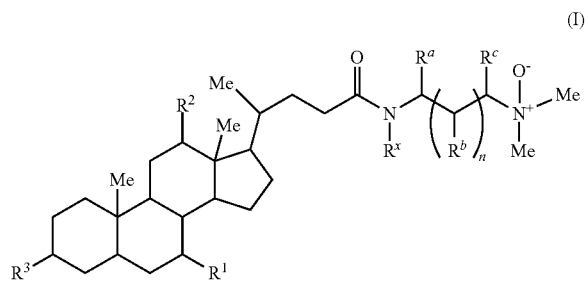

wherein
$R^1$ is H or OH;
$R^2$ is H or OH;
$R^3$ is H or OH;
$R^x$ is H or $C_1$-$C_6$-alkyl;
n is 0, 1, 2, 3, or 4; and
$R^a$, $R^b$, and $R^c$ are each independently H, OH, or $C_1$-$C_6$-alkyl.

2. A compound of claim 1, wherein $R^1$ is H.
3. A compound of claim 1, wherein $R^1$ is OH.
4. A compound of claim 1, wherein $R^2$ is H.
5. A compound claim 1, wherein $R^2$ is OH.
6. A compound of claim 1, wherein $R^3$ is H.
7. A compound of claim 1, wherein $R^3$ is OH.
8. A compound of claim 1, wherein at least one of $R^2$, $R^3$, and $R^4$ is not H.
9. A compound claim 1, wherein $R^x$ is H.
10. A compound of claim 1, wherein $R^x$ is $C_1$-$C_6$-alkyl.
11. A compound of claim 1, wherein each of $R^a$, $R^b$, and $R^c$ is H.
12. A compound of claim 1, wherein at least one of $R^a$, $R^b$, and $R^c$ is not H.
13. A compound of claim 1, wherein at least two of $R^a$, $R^b$, and $R^c$ are not H.
14. A compound of claim 1, wherein "n" is 0.
15. A compound of claim 1, wherein "n" is 1.
16. A compound of claim 1, wherein "n" is 2.
17. A compound of claim 1, wherein "n" is 3.
18. A compound of claim 1, wherein "n" is 4.
19. The compound of claim 1 that is:

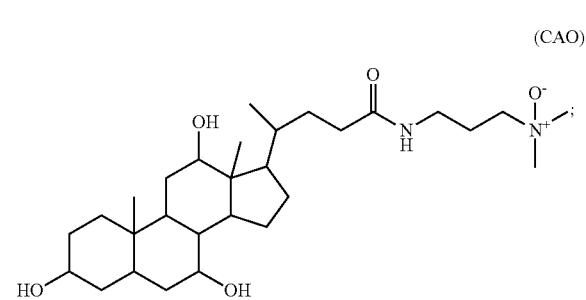

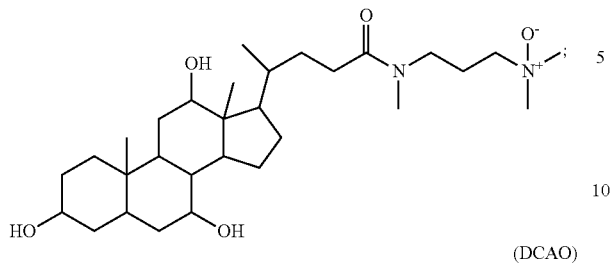
(CAO-1)

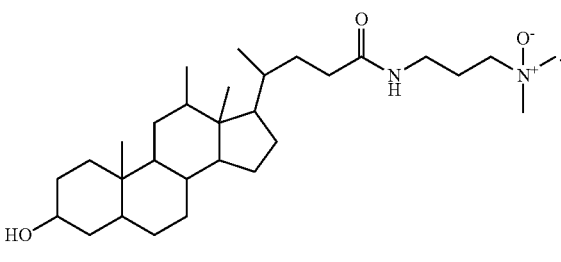
(LCAO)

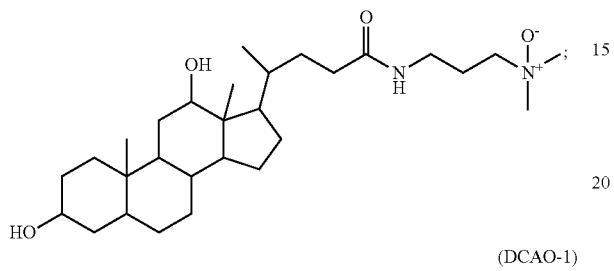
(DCAO)

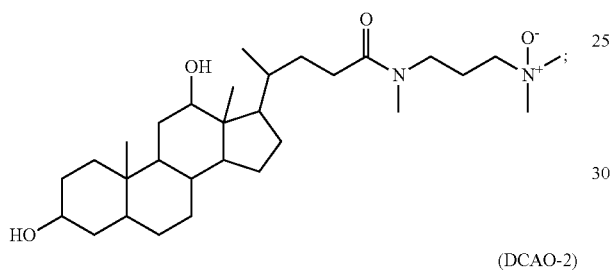
(DCAO-1)

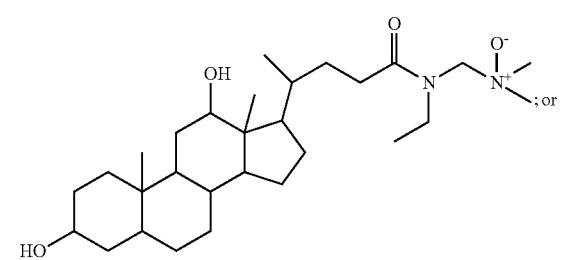
(DCAO-2); or

20. A composition of matter comprising a compound as recited in claim 1, in combination with a membrane protein.

21. The composition of matter claim 20, wherein the membrane protein is an integral membrane protein.

22. A method for solubilizing a protein, the method comprising contacting the protein in an aqueous environment with a solubilizing-effective amount of a compound as recited in claim 1.

23. The method of claim 22, further comprising heating the protein and the compound.

24. The method of claim 22, wherein the solubilizing-effective amount of the compound ranges from about an amount of the compound necessary to achieve its critical micelle concentration, to about ten times the amount of the compound necessary to achieve its critical micelle concentration.

25. A method for purifying a protein, the method comprising:

contacting a protein in an aqueous environment with a solubilizing-effective amount of a compound as recited in claim 1, thereby forming micelles comprising a plurality of the compounds surrounding the protein, and isolating the micelles.

* * * * *